US010253088B2

(12) United States Patent
Wilson et al.

(10) Patent No.: US 10,253,088 B2
(45) Date of Patent: Apr. 9, 2019

(54) MODIFIED VON WILLEBRAND FACTOR

(71) Applicant: CSL Behring Lengnau AG, Lengnau BE (CH)

(72) Inventors: Michael Wilson, Victoria (AU); Steve Dower, Victoria (AU); Dallas Hartman, Victoria (AU); Mathew Hardy, Victoria (AU)

(73) Assignee: CSL Behring Lengnau AG, Lengnau BE (CH)

(*) Notice: Subject to any disclaimer, the term of this patent is extended or adjusted under 35 U.S.C. 154(b) by 0 days.

(21) Appl. No.: 15/323,401

(22) PCT Filed: Jul. 2, 2015

(86) PCT No.: PCT/AU2015/050369
§ 371 (c)(1),
(2) Date: Dec. 30, 2016

(87) PCT Pub. No.: WO2016/000039
PCT Pub. Date: Jan. 7, 2016

(65) Prior Publication Data

US 2017/0152300 A1 Jun. 1, 2017

(30) Foreign Application Priority Data

Jul. 2, 2014 (AU) ................................ 2014902532

(51) Int. Cl.

| | |
|---|---|
| *A61P 7/04* | (2006.01) |
| *A61K 38/00* | (2006.01) |
| *A61K 38/36* | (2006.01) |
| *A61K 38/37* | (2006.01) |
| *C07K 14/755* | (2006.01) |
| *C07K 14/765* | (2006.01) |

(52) U.S. Cl.
CPC ............ *C07K 14/755* (2013.01); *A61K 38/36* (2013.01); *A61K 38/37* (2013.01); *A61P 7/04* (2018.01); *C07K 14/765* (2013.01); *A61K 38/00* (2013.01); *C07K 2319/31* (2013.01)

(58) Field of Classification Search
None
See application file for complete search history.

(56) References Cited

U.S. PATENT DOCUMENTS

| | | | |
|---|---|---|---|
| 4,970,300 | A | 11/1990 | Fulton et al. |
| 5,594,768 | A | 1/1997 | Fujii et al. |
| 6,403,077 | B1 | 6/2002 | Strom et al. |
| 8,575,104 | B2 | 11/2013 | Weimer et al. |
| 2004/0087778 | A1 | 5/2004 | Feige et al. |

FOREIGN PATENT DOCUMENTS

| | | | |
|---|---|---|---|
| EP | 0503991 | A1 | 9/1992 |
| EP | 0784632 | B1 | 1/1999 |
| JP | 07-306165 | | 11/1995 |
| WO | WO 94/15625 | | 7/1994 |
| WO | WO 97/03193 | | 1/1997 |
| WO | WO 97/11957 | | 4/1997 |
| WO | WO 97/40145 | | 10/1997 |
| WO | WO 99/55306 | | 11/1999 |
| WO | WO 02/060951 | A2 | 8/2002 |
| WO | WO 02/103024 | A2 | 12/2002 |
| WO | WO 03/076567 | A2 | 9/2003 |
| WO | WO 03/087355 | A1 | 10/2003 |
| WO | WO 03/093313 | A2 | 11/2003 |
| WO | WO 2004/075293 | A2 | 9/2004 |
| WO | WO 2004/101740 | A2 | 11/2004 |
| WO | WO 2005/000892 | A2 | 1/2005 |
| WO | WO 2005/001025 | A2 | 1/2005 |
| WO | WO 2005/063808 | A1 | 7/2005 |
| WO | WO 2006/000448 | A2 | 1/2006 |
| WO | WO 2006/053299 | A2 | 5/2006 |
| WO | WO 2006/071801 | A2 | 7/2006 |
| WO | WO 2006/108590 | A1 | 10/2006 |
| WO | WO 2007/090584 | A1 | 8/2007 |
| WO | WO 2007/126808 | A1 | 11/2007 |
| WO | WO 2007/144173 | A1 | 12/2007 |
| WO | WO 2008/077616 | A1 | 7/2008 |
| WO | WO 2009/1561367 | A1 | 12/2009 |
| WO | WO 2013/120939 | A1 | 8/2013 |

OTHER PUBLICATIONS

Office Action issued by the China Patent and Trademark Office in corresponding Chinese Application No. 201480077101.7, dated Apr. 19, 2017 (14 pages).
Rizza, C.R. et al., Coagulation Assay of VIIIC and IXC, The Hemophilias, (1982), pp. 18-38.
Rosén, S., Assay of Factor VIII:C with a Chromogenic Substrate, Scand J Haematol—Suppl. 40, vol. 33, pp. 139-145 (1984).
Collins, C.J., et al., Molecular cloning of the human gene for von Willebrand factor and identification of the transcription initiation site, Proc. Natl. Acad. Sci. vol. 84, pp. 4393-4397 (1987).
Kaufman, R.J., Effect of von Willebrand Factor Coexpression on the synthesis and Secretion of Factor VIII in Chinese Hamster Ovary Cells, Molecular and Cellular Biology, pp. 1233-1242 (1989).
Fischer, B., et al., Structural analysis of recombinant von Wilebrand factor: identification of hetero-and homo-dimers, FEBS Letters, 351, pp. 345-348 (1994).
Vlot, A.J., et al., The Affinity and Stoichiometry of Binding of Human Factor VIII to von Willebrand Factor, Blood, vol. 85, No. 11, pp. 3150-3157 (1995).

(Continued)

*Primary Examiner* — Christina Bradley
(74) *Attorney, Agent, or Firm* — Finnegan, Henderson, Farabow, Garrett & Dunner, L.L.P.

(57) ABSTRACT

The present invention provides a modified polypeptide which binds Factor VIII. The modified polypeptide comprises a sequence as shown in SEQ ID NO:3 in which the sequence comprises at least a modification at position 1 or 3 such that the modified polypeptide binds to Factor VIII with an off rate at least 5 fold lower than a reference polypeptide comprising an unmodified SEQ ID NO:3.

8 Claims, No Drawings

Specification includes a Sequence Listing.

(56) References Cited

OTHER PUBLICATIONS

Swaroop, M., et al., Mutagenesis of a Potential Immunoglobulin-binding Protein-binding Site Enhances Secretion of Coagulation Factor VIII, The Journal of Biological Chemistry, vol. 272, No. 39, pp. 24121-24124 (1997).
Amano, K., et al., Mutation at either Arg336 or Arg562 in Factor VIII Is Sufficient for Complete Resistance to Activated Protein C (APC)-mediated Inactivation: Implications for the APC Resistance Test, Thromb Haemost, vol. 79, pp. 557-563 (1998).
Lollar, P., Characterization of Factor VIII B-Cell Inhibitory Epitopes, Thrombosis and Haemostasis, vol. 82(2), pp. 505-508 (1999).
Oh, S.H., et al., Synthesis of recombinant blood coagulation factor VII (FVIII) heavy and light chains and reconstitution of active form of FVIII, Experimental and Molecular Medicine, vol. 31, No. 2, pp. 95-100 (1990).
Frokjaer, S., et al., Pharmaceutical Formulation, Development of Peptides and Proteins, Taylor & Francis, Abstract Review (1 page).
Gennaro, A., Remington The Science and Practice of Pharmacy, 20$^{th}$ Ed., Lippincottt Williams & Wilkins (2000), Table of Contents, 4 pages.
Product details for Wadem A., et al., Handbook of Pharmaceutical Excipients, Amer Pharmaceuical Assn., 3$^{rd}$ Ed. (2000), 1 page.
Ananyeva, N. M., et al., Catabolism of the Coagulation Factor VIII, TCM vol. 11, No. 6, pp. 251-257 (2001).
Kallas, A., et al., The von Willebrand factor of collagen-binding activity assay: clinical application, Ann Hematol, vol. 80, pp. 446-471 (2001).
Federici, A.B., et al., A sensitive ristocetin co-factor activity assay with recombinant glycoprotein Ibα for the diagnosis of patients with low von Willebrand factor levels, Haematologica, vol. 89(1), pp. 77-85 (2004).
Milao, H.Z., Bioengineering of coagulation facto VII for improved secretion, Blood (2004) vol. 103, pp. 3412-3419.
Pipe, S.W., Coagulation Factors with Improved Properties for Hemophilia Gene Therapy, Seminars in Thrombosis and Hemostasis, vol. 30, No. 2 (2004) pp. 227-237.
Wakabayashi, H., et al., A Glu 113 Ala Mutation within a Factor VIII Ca$^{2+}$-Binding Site Enhances Cofactor Interactions in Factor Xase, Biochemistry, vol. 44 (2005), pp. 10298-10304.
Dumont, J.A., Monomeric FC Fusions Impact on Pharmacokinetic and Biological Activity of Protein Therapeutics, Biodrugs, vol. 20(3), pp. 151-160 (2006).
Gale, A.J., et al., Intrinsic stability and functional properties of disulfide bond-stabilized coagulation factor VIIIa variants, Journal of Thrombosis and Hemostasis, vol. 4, pp. 1315-1322 (2006).
Sucker, C., et al., Determination of von Willebrand Factor Activity: Evaluation of the HaemosIL™ Assay in Comparison With Established Procedures, Clinical and Applied Thrombasis/Hemostasis, vol. 12, No. 3, pp. 305-310 (2006).
Zhou, Y.F., et al., Sequence and structure relationship within von Willebrand factor, Blood, vol. 120, No. 2, pp. 449-458 (2012).
Zollner, S.B., Preclinical efficacy and safety of rVIII-SingleChain (CSL627), a novel recombinant single-chain factor VIII, Thrombosis Research, vol. 132, pp. 280-287 (2013).
Jorieux, S., et al., Conformational charges in the D' domain of von Willebrand factor induced by CYS 25 and CYS 95 mutations lead to factor VIII binding defect and multimeric impairment, Hemostasis, Thrombosis, and Vascular Biology, Blood, vol. 95, No. 10, pp. 3139-3145 (2000).
Hilbert, L., et al., Two novel mutations, Q1053H and C1060R, located in the D3 domain of von Willebrand factor, are responsible for decreased FVIII-binding capacity, British Journal of Hematology, vol. 120, pp. 627-632 (2003).
International Search Report, issued in International Application No. PCT/AU2015/050369, dated Aug. 27, 2015 (5 pages).
Writien Opinion of the International Searching Authority, issued in International Application No. PCT/AU2015/050369, dated Aug. 27, 2015 (4 pages).

MODIFIED VON WILLEBRAND FACTOR

CROSS-REFERENCES TO RELATED APPLICATIONS

This application is a U.S. national phase application of International PCT Patent Application No. PCT/AU2015/050369, which was filed on Jul. 2, 2015, which claims priority to Australian Patent Application No. 2014902532, filed Jul. 2, 2014. These applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is DAVI_045_01US_ST25.txt. The text file is 104 KB, was created on Dec. 30, 2016, and is being submitted electronically via EFS-Web.

FIELD OF THE INVENTION

The present invention relates to polypeptides, in particular modified von Willebrand Factor which exhibit improved binding affinity to Factor VIII. The invention further relates to a complex comprising the polypeptide and FVIII, to a polynucleotide encoding the polypeptide of the invention and a method of producing the polypeptide. Furthermore, the invention concerns the therapeutic or prophylactic use of the polypeptide or complex of the invention for treating bleeding disorders.

BACKGROUND OF THE INVENTION

There are various bleeding disorders caused by deficiencies of blood coagulation factors. The most common disorders are hemophilia A and B, resulting from deficiencies of blood coagulation factor VIII and IX, respectively. Another known bleeding disorder is von Willebrand's disease.

In plasma FVIII exists predominantly in a noncovalent complex with VWF and acts as a cofactor for activated factor IX in the membrane bound activated factor X generating complex.

Several attempts have been made to prolong the half-life of non-activated FVIII either by reducing its interaction with cellular receptors (WO 03/093313A2, WO 02/060951A2), by covalently attaching polymers to FVIII (WO 94/15625, WO 97/11957 and U.S. Pat. No. 4,970,300), by encapsulation of FVIII (WO 99/55306), by introduction of novel metal binding sites (WO 97/03193), by covalently attaching the A2 domain to the A3 domain either by peptidic (WO 97/40145 and WO 03/087355) or disulfide linkage (WO 02/103024A2) or by covalently attaching the A1 domain to the A2 domain (WO2006/108590).

Another approach to enhance the functional half-life of FVIII or VWF is by PEGylation of FVIII (WO 2007/126808, WO 2006/053299, WO 2004/075923). PEGylation of VWF (WO 2006/071801) has also been attempted in an effort to indirectly enhance the half-life of FVIII present in plasma. Also fusion proteins of FVIII have been described (WO 2004/101740, WO2008/077616 and WO 2009/156137).

VWF, which is missing, functionally defective or only available in reduced quantity in different forms of von Willebrand disease (VWD), is a multimeric adhesive glycoprotein present in plasma, which has multiple physiological functions. During primary hemostasis VWF acts as a mediator between specific receptors on the platelet surface and components of the extracellular matrix such as collagen. Moreover, VWF serves as a carrier and stabilizing protein for procoagulant FVIII. VWF is synthesized in endothelial cells and megakaryocytes as a 2813 amino acid precursor molecule. The amino acid sequence and the cDNA sequence of wild-type VWF are disclosed in Collins et al. 1987, Proc Natl. Acad. Sci. USA 84:4393-4397. The precursor polypeptide, pre-pro-VWF, consists of a 22-residue signal peptide, a 741-residue pro-peptide and the 2050-residue polypeptide found in plasma (Fischer et al., FEBS Lett. 351: 345-348, 1994). After cleavage of the signal peptide in the endoplasmic reticulum a C-terminal disulfide bridge is formed between two monomers of VWF. During further transport through the secretory pathway 12 N-linked and 10 O-linked carbohydrate side chains are added. Importantly, VWF dimers are multimerized via N-terminal disulfide bridges and the propeptide of 741 amino acids is cleaved off by the enzyme PACE/furin in the late Golgi apparatus. The propeptide as well as the high-molecular-weight multimers of VWF (VWF-HMWM) are stored in the Weibel-Pallade bodies of endothelial cells or in the α-Granules of platelets.

Once secreted into plasma the protease ADAMTS13 cleaves VWF within the A1 domain of VWF. Plasma VWF consists of a range of multimers ranging from single dimers of 500 kDa to multimers consisting of more than 20 dimers of a molecular weight of over 10,000 kDa. Typically VWF high molecular weight multimers (VWF-HMWM) have the strongest hemostatic activity, which can be measured in ristocetin cofactor activity (VWF:RCo). The higher the ratio of VWF:RCo/VWF antigen, the higher the relative amount of high molecular weight multimers.

Defects in VWF are causal to von Willebrand disease (VWD), which is characterized by a more or less pronounced bleeding phenotype. VWD type 3 is the most severe form in which VWF is completely missing, VWD type 1 relates to a quantitative loss of VWF and its phenotype can be very mild. VWD type 2 relates to qualitative defects of VWF and can be as severe as VWD type 3. VWD type 2 has many sub forms some of them being associated with the loss or the decrease of high molecular weight multimers. Von VWD type 2a is characterized by a loss of both intermediate and large multimers. VWD type 2B is characterized by a loss of highest-molecular-weight multimers.

VWD is the most frequent inherited bleeding disorder in humans and can be treated by replacement therapy with concentrates containing VWF of plasma or recombinant origin. VWF can be prepared from human plasma as for example described in EP 05503991. EP 0784632 describes a method for producing and isolating recombinant VWF.

In plasma FVIII binds with high affinity to VWF, which protects it from premature catabolism and thus, plays in addition to its role in primary hemostasis, a crucial role in regulation of plasma levels of FVIII and as a consequence is also a central factor in the control of secondary hemostasis. The half-life of non-activated FVIII bound to VWF is about 12 to 14 hours in plasma. In von Willebrand disease type 3, where no or almost no VWF is present, the half-life of FVIII is only about 6 hours, leading to symptoms of mild to moderate hemophilia A in such patients due to decreased concentrations of FVIII. The stabilizing effect of VWF on FVIII has also been used to aid recombinant expression of FVIII in CHO cells (Kaufman et al. 1989, Mol Cell Biol).

SUMMARY OF THE INVENTION

In a first aspect the present invention provides a modified polypeptide which binds Factor VIII wherein the modified polypeptide comprises a sequence as shown in SEQ ID NO:3 in which the sequence comprises at least a modification at position 1 or 3 such that the modified polypeptide binds to Factor VIII with an off rate at least 5 fold lower than a reference polypeptide comprising an unmodified SEQ ID NO:3.

In a second aspect the present invention provides a modified polypeptide which binds Factor VIII wherein the modified polypeptide comprises a sequence as shown in SEQ ID NO:3 in which the sequence comprises a modification at at least position 3 such that the modified polypeptide binds to Factor VIII with an off rate lower than a reference polypeptide comprising an unmodified SEQ ID NO:3.

In a third aspect the present invention provides a modified polypeptide which binds Factor VIII wherein the modified polypeptide comprises a sequence as shown in SEQ ID NO:3 in which the sequence comprises a modification at at least position 1 such that the modified polypeptide binds to Factor VIII with an off rate lower than a reference polypeptide comprising an unmodified SEQ ID NO:3, wherein the residue at position 1 is selected from the group consisting of G, P, E, Y, A and L.

The present invention also provides a complex comprising a Factor VIII molecule and the modified polypeptide of the present invention and a polynucleotide encoding the modified polypeptide.

The present invention also provides a method of increasing the Factor VIII binding affinity of VWF, comprising introducing at least two mutations into the D' domain of the VWF amino acid sequence such that the residues at positions 1 and 3 or positions 3 and 9 or positions 3 and 43 of SEQ ID NO:3 are altered.

DETAILED DESCRIPTION

VWF

The term "von Willebrand Factor" or "VWF", as used herein, refers to any polypeptide having a biological activity of wild type VWF, in particular the ability to bind Factor VIII. The gene encoding wild type VWF is transcribed into a 9 kb mRNA which is translated into a pre-propolypeptide of 2813 amino acids with an estimated molecular weight of 310,000 Da. The pre-propolypeptide contains a 22 amino acids signal peptide, a 741 amino acid pro-polypeptide and the mature subunit. Cleavage of the 741 amino acids propolypeptide from the N-terminus results in mature VWF consisting of 2050 amino acids. The amino acid sequence of the VWF pre-propolypeptide is shown in SEQ ID NO:2. Unless indicated otherwise, the amino acid numbering of VWF residues in this application refers to SEQ ID NO:2, even if the VWF molecule does not need to comprise all residues of SEQ ID NO:2. The amino acid sequence of mature VWF is shown in SEQ ID NO:4. The term "VWF" as used herein refers to the mature form of VWF unless indicated otherwise.

The propolypeptide of wild type VWF comprises multiple domains which are arranged in the following order:

D1-D2-D'-D3-A1-A2-A3-D4-B1-B2-B3-C1-C2-CK

The D1 and D2 domain represent the propeptide which is cleaved off to yield the mature VWF. The D' domain encompasses amino acids 764 to 865 of SEQ ID NO:2. The amino acid sequence of the D' domain of wild type VWF is shown in SEQ ID NO:3. The carboxy terminal 90 residues comprise the "CK" domain that is homologous to the "cysteine knot" superfamily of protein. These family members have a tendency to dimerise through disulfide bonds.

Preferably, wild type VWF comprises the amino acid sequence of mature VWF as shown in SEQ ID NO:4. Also encompassed are additions, insertions, N-terminal, C-terminal or internal deletions of VWF as long as a biological activity of VWF, in particular the ability to bind FVIII, is retained. The biological activity is retained in the sense of the invention if the VWF with deletions retains at least 10%, preferably at least 25%, more preferably at least 50%, most preferably at least 75% of the biological activity of wild-type VWF. The biological activity of wild-type VWF can be determined by the artisan using methods for ristocetin co-factor activity (Federici A B et al. 2004. Haematologica 89:77-85), binding of VWF to GP Ibα of the platelet glycoprotein complex Ib-V-IX (Sucker et al. 2006. Clin Appl Thromb Hemost. 12:305-310), or a collagen binding assay (Kallas & Talpsep. 2001. Annals of Hematology 80:466-471). Where the biological activity of VWF is the ability to bind FVIII this can be measured in a number of ways, however, it is preferably measured as described in Example 1 herein.

Factor VIII

The terms "blood coagulation Factor VIII", "Factor VIII" and "FVIII" are used interchangeably herein. "Blood coagulation Factor VIII" includes wild-type blood coagulation FVIII as well as derivatives of wild-type blood coagulation FVIII having the procoagulant activity of wild-type blood coagulation FVIII. Derivatives may have deletions, insertions and/or additions compared with the amino acid sequence of wild-type FVIII. The term FVIII includes proteolytically processed forms of FVIII, e.g. the form before activation, comprising heavy chain and light chain.

The term "FVIII" includes any FVIII variants or mutants having at least 25%, more preferably at least 50%, most preferably at least 75% of the biological activity of wild-type factor VIII.

As non-limiting examples, FVIII molecules include FVIII mutants preventing or reducing APC cleavage (Amano 1998. Thromb. Haemost. 79:557-563), FVIII mutants further stabilizing the A2 domain (WO 97/40145), FVIII mutants having increased expression (Swaroop et al. 1997. JBC 272:24121-24124), FVIII mutants having reduced immunogenicity (Lollar 1999. Thromb. Haemost. 82:505-508), FVIII reconstituted from differently expressed heavy and light chains (Oh et al. 1999. Exp. Mol. Med. 31:95-100), FVIII mutants having reduced binding to receptors leading to catabolism of FVIII like HSPG (heparan sulfate proteoglycans) and/or LRP (low density lipoprotein receptor related protein) (Ananyeva et al. 2001. TCM, 11:251-257), disulfide bond-stabilized FVIII variants (Gale et al., 2006. J. Thromb. Hemost. 4:1315-1322), FVIII mutants with improved secretion properties (Miao et al., 2004. Blood 103:3412-3419), FVIII mutants with increased cofactor specific activity (Wakabayashi et al., 2005. Biochemistry 44:10298-304), FVIII mutants with improved biosynthesis and secretion, reduced ER chaperone interaction, improved ER-Golgi transport, increased activation or resistance to inactivation and improved half-life (summarized by Pipe 2004. Sem. Thromb. Hemost. 30:227-237). Another particularly preferred example is a recombinant form of FVIII as described in Zollner et al 2013, Thrombosis Research, 132:280-287. All of these FVIII mutants and variants are incorporated herein by reference in their entirety.

Preferably FVIII comprises the full length sequence of FVIII as shown in SEQ ID NO:18. Also encompassed are additions, insertions, substitutions, N-terminal, C-terminal or internal deletions of FVIII as long as the biological activity of FVIII is retained. The biological activity is retained in the sense of the invention if the FVIII with modifications retains at least 10%, preferably at least 25%, more preferably at least 50%, most preferably at least 75% of the biological activity of wild-type FVIII. The biological activity of FVIII can be determined by the artisan as described below.

A suitable test to determine the biological activity of FVIII is for example the one stage or the two stage coagulation assay (Rizza et al. 1982. Coagulation assay of FVIII:C and FIXa in Bloom ed. The Hemophilias. NY Churchchill Livingston 1992) or the chromogenic substrate FVIII:C assay (S. Rosen, 1984. Scand J Haematol 33: 139-145, suppl.). The content of these references is incorporated herein by reference.

The amino acid sequence of the mature wild-type form of human blood coagulation FVIII is shown in SEQ ID NO: 18. The reference to an amino acid position of a specific sequence means the position of said amino acid in the FVIII wild-type protein and does not exclude the presence of mutations, e.g. deletions, insertions and/or substitutions at other positions in the sequence referred to. For example, a mutation in "Glu2004" referring to SEQ ID NO: 18 does not exclude that in the modified homologue one or more amino acids at positions 1 through 2332 of SEQ ID NO: 18 are missing.

"FVIII" and/or "VWF" within the above definition also include natural allelic variations that may exist and occur from one individual to another. "FVIII" and/or "VWF" within the above definition further includes variants of FVIII and/or VWF. Such variants differ in one or more amino acid residues from the wild-type sequence. Examples of such differences may include conservative amino acid substitutions, i.e. substitutions within groups of amino acids with similar characteristics, e.g. (1) small amino acids, (2) acidic amino acids, (3) polar amino acids, (4) basic amino acids, (5) hydrophobic amino acids, and (6) aromatic amino acids. Examples of such conservative substitutions are shown in Table 1.

TABLE 1

| (1) | Alanine | Glycine | | |
|---|---|---|---|---|
| (2) | Aspartic acid | Glutamic acid | | |
| (3) | Asparagine | Glutamine | Serine | Threonine |
| (4) | Arginine | Histidine | Lysine | |
| (5) | Isoleucine | Leucine | Methionine | Valine |
| (6) | Phenylalanine | Tyrosine | Tryptophan | |

Modified VWF

The modified VWF of the present invention has an amino acid sequence which differs from that of wild-type VWF. According to the present invention the modified VWF has at least one amino acid substitution within its D' domain, as compared to the amino acid sequence of the D' domain of wild-type VWF as shown in SEQ ID NO:3.

The amino acid sequence of the D' domain of the modified VWF can have one or more amino acid substitutions relative to SEQ ID NO:3. The amino acid sequence of the D' domain of the modified VWF preferably has one or 2 amino acid substitutions relative to SEQ ID NO:3.

It is preferred that S at position 1 of SEQ ID NO:3 is substituted with an amino acid selected from the group consisting of G, P, V, E, Y, A and L.

It is also preferred that S at position 3 of SEQ ID NO:3 is substituted with an amino acid selected from the group consisting of Y, I, M, V, F, H, R and W.

Preferred combinations of substitutions include S764G/S766Y, S764P/S766I, S764P/S766M, S764V/S766Y, S764E/S766Y, S764Y/S766Y, S764L/S766Y, S764P/S766W, S766W/S806A, S766Y/P769K, S766Y/P769N, S766Y/P769R and S764P/S766L.

According to an aspect of this invention the binding affinity of the polypeptide of the present invention to FVIII is higher than that of a reference polypeptide which has the same amino acid sequence except for the modification in SEQ ID NO:3.

The binding affinity of a VWF molecule to a Factor VIII molecule can be determined by a binding assay used in the art. For example, the VWF molecule may be immobilized on a solid support, increasing concentrations of Factor VIII are applied, incubated for a certain period of time, and after washing, bound Factor VIII is determined with a chromogenic assay. The affinity constant or dissociation constant may then be determined by Scatchard analysis or another suitable method. A method of determining the affinity of binding of human Factor VIII to von Willebrand Factor are described in Vlot et al. (1995), Blood, Volume 85, Number 11, 3150-3157. Preferably, however, the affinity of VWF to Factor VIII is determined as described in Example 1 of this application.

Any indication herein of affinity, including dissociation constants, preferably refers to the binding of the modified VWF of the invention, or of the polypeptide of the invention to FVIII. The amino acid sequence of single chain of FVIII is shown in SEQ ID NO:14.

As the interaction of VWF with FVIII typically has a high on-rate, changes in the dissociation constant is largely dependent on changes in the off-rate. Accordingly the main focus in increasing the association of VWF with FVIII involves efforts to decrease the off-rate between FVIII and VWF. Preferably the off-rate of the modified VWF and FVIII in comparison to wild type VWF and FVIII is at least two fold lower, more preferably at least 5 fold lower, preferably at least 10 fold lower and more preferably at least 20 fold lower.

The dissociation constant of the complex consisting of VWF and FVIII is preferably 0.2 nmol/L or less, more preferably 0.175 nmol/L or less, more preferably 0.15 nmol/L or less, more preferably 0.125 nmol/L or less, more preferably 0.1 nmol/L or less, more preferably 0.05 nmol/L or less, most preferably 0.01 nmol/L or less.

The dissociation constant KD of a complex of the polypeptide of the invention and the Factor VIII of SEQ ID NO:13 is typically less than 90% of the dissociation constant KD of a complex of the reference polypeptide (e.g. the polypeptide of SEQ ID NO:4) and the Factor VIII of SEQ ID NO:13. The dissociation constant KD of a complex of the polypeptide of the invention and the Factor VIII of SEQ ID NO:13 is preferably less than 75%, more preferably less than 50%, more preferably less than 25%, more preferably less than 10%, more preferably less than 5%, of the dissociation constant KD of a complex of the reference polypeptide (e.g. the polypeptide of SEQ ID NO:4) and the Factor VIII of SEQ ID NO:13.

The reference polypeptide is a polypeptide the amino acid sequence of which is identical to that of the polypeptide of the present invention except for the mutation within the D' domain of VWF. That is, the reference polypeptide preferably has an amino acid sequence identical to that of the polypeptide of the present invention, with the proviso that the D' domain in the reference polypeptide consists of the amino acid sequence as shown in SEQ ID NO:3. In other words, the only difference in sequence between the polypeptide of the invention and the reference polypeptide lies in the amino acid sequence of the D' domain. The reference polypeptide has preferably been prepared under the same conditions as the polypeptide of the invention.

The polypeptide of the present invention may consist of the modified VWF. In another embodiment, the polypeptide of the present invention comprises a further amino acid sequence, preferably a heterologous amino acid sequence. The heterologous amino acid sequence is typically not fused to VWF in nature.

The present invention is particularly useful in cases where a VWF variant is used having an improved half-life. This can be achieved for example by fusing VWF to human serum albumin. A detailed discussion of such fusions is provided in U.S. Pat. No. 8,575,104, the disclosure of which is incorporated herein by reference.

In one embodiment, the polypeptide of the present invention comprises the modified VWF and a half-life enhancing protein (HLEP). Preferably, the HLEP is an albumin.

One or more HLEPs may be fused to the C-terminal part of VWF preferably as not to interfere with the binding capabilities of VWF for example to FVIII, platelets, heparin or collagen.

In one embodiment the modified VWF has the following structure:

$$\text{N-VWF-C-L1-H,} \qquad \text{[formula 1]}$$

wherein
N is an N-terminal part of VWF,
L1 is a chemical bond or a linker sequence
H is a HLEP, and
C is a C-terminal part of VWF L1 may be a chemical bond or a linker sequence consisting of one or more amino acids, e.g. of 1 to 50, 1 to 30, 1 to 20, 1 to 15, 1 to 10, 1 to 5 or 1 to 3 (e.g. 1, 2 or 3) amino acids and which may be equal or different from each other. Usually, the linker sequences are not present at the corresponding position in the wild-type coagulation factor. Examples of suitable amino acids present in L1 include Gly and Ser.

Preferred HLEP sequences are described infra. Likewise encompassed by the invention are fusions to the exact "N-terminal amino acid" of the respective HLEP, or fusions to the "N-terminal part" of the respective HLEP, which includes N-terminal deletions of one or more amino acids of the HLEP.

The modified VWF or the complex of the FVIII with the modified VWF of the invention may comprise more than one HLEP sequence, e.g. two or three HLEP sequences. These multiple HLEP sequences may be fused to the C-terminal part of VWF in tandem, e.g. as successive repeats.

Linker Sequences

According to this invention, the therapeutic polypeptide moiety may be coupled to the HLEP moiety by a peptide linker. The linker should be non-immunogenic and may be a non-cleavable or cleavable linker.

Non-cleavable linkers may be comprised of alternating glycine and serine residues as exemplified in WO2007/090584.

In another embodiment of the invention the peptidic linker between the VWF moiety and the albumin moiety consists of peptide sequences, which serve as natural inter-domain linkers in human proteins. Preferably such peptide sequences in their natural environment are located close to the protein surface and are accessible to the immune system so that one can assume a natural tolerance against this sequence. Examples are given in WO2007/090584.

Cleavable linkers should be flexible enough to allow cleavage by proteases. In a preferred embodiment the cleavage of the linker proceeds comparably fast as the activation of FVIII within the fusion protein, if the fusion protein is a modified FVIII.

The cleavable linker preferably comprises a sequence derived from
(a) the therapeutic polypeptide to be administered itself if it contains proteolytic cleavage sites that are proteolytically cleaved during activation of the therapeutic polypeptide,
(b) a substrate polypeptide cleaved by a protease which is activated or formed by the involvement of the therapeutic polypeptide, or
(c) a polypeptide involved in coagulation or fibrinolysis.

The linker region in a more preferred embodiment comprises a sequence of VWF, which should result in a decreased risk of neoantigenic properties of the expressed fusion protein.

The linker peptides are preferably cleavable by the proteases of the coagulation system, for example FIIa, FIXa, FXa, FXIa, FXIIa and FVIIa.

Exemplary combinations of therapeutic polypeptide, cleavable linker and HLEP include the constructs listed in WO2007/090584 (for example in table 2 and FIG. 4) and WO2007/144173 (for example in table 3a and 3b), but are not limited to these.

Half-Life Enhancing Polypeptides (HLEPs)

A "half-life enhancing polypeptide" as used herein is selected from the group consisting of albumin, a member of the albumin-family, the constant region of immunoglobulin G and fragments thereof, region and polypeptides capable of binding under physiological conditions to albumin, to members of the albumin family as well as to portions of an immunoglobulin constant region. It may be a full-length half-life-enhancing protein described herein (e.g. albumin, a member of the albumin-family or the constant region of immunoglobulin G) or one or more fragments thereof that are capable of stabilizing or prolonging the therapeutic activity or the biological activity of the coagulation factor. Such fragments may be of 10 or more amino acids in length or may include at least about 15, at least about 20, at least about 25, at least about 30, at least about 50, at least about 100, or more contiguous amino acids from the HLEP sequence or may include part or all of specific domains of the respective HLEP, as long as the HLEP fragment provides a functional half-life extension of at least 25% compared to a wild-type VWF.

The HLEP portion of the proposed coagulation factor insertion constructs of the invention may be a variant of a normal HLEP. The term "variants" includes insertions, deletions and substitutions, either conservative or non-conservative, where such changes do not substantially alter the active site, or active domain which confers the biological activities of the modified VWF.

In particular, the proposed VWF HLEP fusion constructs of the invention may include naturally occurring polymorphic variants of HLEPs and fragments of HLEPs. The HLEP may be derived from any vertebrate, especially any mammal, for example human, monkey, cow, sheep, or pig. Non-mammalian HLEPs include, but are not limited to, hen and salmon.

Albumin as HLEP

The terms, "human serum albumin" (HSA) and "human albumin" (HA) and "albumin" (ALB) are used interchangeably in this application. The terms "albumin" and "serum albumin" are broader, and encompass human serum albumin (and fragments and variants thereof) as well as albumin from other species (and fragments and variants thereof).

As used herein, "albumin" refers collectively to albumin polypeptide or amino acid sequence, or an albumin fragment or variant, having one or more functional activities (e.g., biological activities) of albumin. In particular, "albumin" refers to human albumin or fragments thereof, especially the mature form of human albumin as shown in SEQ ID NO:15 herein or albumin from other vertebrates or fragments thereof, or analogs or variants of these molecules or fragments thereof.

In particular, the proposed VWF fusion constructs of the invention may include naturally occurring polymorphic variants of human albumin and fragments of human albumin. Generally speaking, an albumin fragment or variant will be at least 10, preferably at least 40, most preferably more than 70 amino acids long. The albumin variant may preferentially consist of or alternatively comprise at least one whole domain of albumin or fragments of said domains, for example domains 1 (amino acids 1-194 of SEQ ID NO:15), 2 (amino acids 195-387 of SEQ ID NO: 15), 3 (amino acids 388-585 of SEQ ID NO: 15), 1+2 (1-387 of SEQ ID NO: 15), 2+3 (195-585 of SEQ ID NO: 15) or 1+3 (amino acids 1-194 of SEQ ID NO: 15+ amino acids 388-585 of SEQ ID NO: 15). Each domain is itself made up of two homologous subdomains namely 1-105, 120-194, 195-291, 316-387, 388-491 and 512-585, with flexible intersubdomain linker regions comprising residues Lys106 to Glu119, Glu292 to Val315 and Glu492 to Ala511.

The albumin portion of the proposed VWF fusion constructs of the invention may comprise at least one subdomain or domain of HA or conservative modifications thereof.

In a preferred embodiment the N-terminus of albumin is fused to the C-terminus of the amino acid sequence of the modified VWF. That is, the polypeptide of the present invention may have the structure:

N-mVWF-C-L1-A, wherein N is an N-terminal part of VWF, mVWF is the modified VWF as described hereinabove, C is a C-terminal part of VWF, L1 is a chemical bond or a linker sequence and A is albumin as defined hereinabove.

Immunoglobulins as HLEPs

Immunoglobulin G (IgG) constant regions (Fc) are known in the art to increase the half-life of therapeutic proteins (Dumont J A et al. 2006. BioDrugs 20:151-160). The IgG constant region of the heavy chain consists of 3 domains (CH1-CH3) and a hinge region. The immunoglobulin sequence may be derived from any mammal, or from subclasses IgG1, IgG2, IgG3 or IgG4, respectively. IgG and IgG fragments without an antigen-binding domain may also be used as HLEPs. The therapeutic polypeptide portion is connected to the IgG or the IgG fragments preferably via the hinge region of the antibody or a peptidic linker, which may even be cleavable. Several patents and patent applications describe the fusion of therapeutic proteins to immunoglobulin constant regions to enhance the therapeutic protein's in vivo half-life. US 2004/0087778 and WO 2005/001025 describe fusion proteins of Fc domains or at least portions of immunoglobulin constant regions with biologically active peptides that increase the half-life of the peptide, which otherwise would be quickly eliminated in vivo. Fc-IFN-ß fusion proteins were described that achieved enhanced biological activity, prolonged circulating half-life and greater solubility (WO 2006/000448). Fc-EPO proteins with a prolonged serum half-life and increased in vivo potency were disclosed (WO 2005/063808) as well as Fc fusions with G-CSF (WO 2003/076567), glucagon-like peptide-1 (WO 2005/000892), clotting factors (WO 2004/101740) and interleukin-10 (U.S. Pat. No. 6,403,077), all with half-life enhancing properties.

In another embodiment, the functional half-life of polypeptide of the invention or of FVIII complexed with the polypeptide of the invention is prolonged compared to that of wild type VWF or to that of FVIII complexed with wild type VWF, or with the reference polypeptide as defined supra. The increase may be more than 15%, for example at least 20% or at least 50%. Again, such functional half-life values can be measured in vitro in blood samples taken at different time intervals from said mammal after the modified VWF or the complex of FVIII with modified VWF has been administered.

In another embodiment of the invention, the polypeptide of the invention or FVIII complexed with the polypeptide of the invention exhibits an improved in vivo recovery compared to wild type VWF or to FVIII complexed with wild type VWF, or with the reference polypeptide defined supra. The in vivo recovery can be determined in vivo for example in normal animals or in animal models of hemophilia A, like FVIII knockout mice in which one would expect an increased percentage of FVIII be found by antigen or activity assays in the circulation shortly (5 to 10 min.) after i.v. administration compared to the corresponding wild-type VWF, or reference polypeptide defined supra.

The in vivo recovery is preferably increased by at least 10%, more preferably by at least 20%, and even more preferably by at least 40% compared to FVIII complexed with wild-type VWF, or with the reference polypeptide defined supra.

In yet another embodiment of the invention immunoglobulin constant regions or portions thereof are used as HLEPs. Preferably the Fc region comprised of a CH2 and CH3 domain and a hinge region of an IgG, more preferably of an IgG1 or fragments or variants thereof are used, variants including mutations which enhance binding to the neonatal Fc receptor (FcRn).

Polynucleotides

The invention further relates to a polynucleotide encoding a modified VWF or a polypeptide comprising said modified VWF, as described in this application. The term "polynucleotide(s)" generally refers to any polyribonucleotide or polydeoxyribonucleotide that may be unmodified RNA or DNA or modified RNA or DNA. The polynucleotide may be single- or double-stranded DNA, single or double-stranded RNA. As used herein, the term "polynucleotide(s)" also includes DNAs or RNAs that comprise one or more modified bases and/or unusual bases, such as inosine. It will be appreciated that a variety of modifications may be made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells.

The skilled person will understand that, due to the degeneracy of the genetic code, a given polypeptide can be encoded by different polynucleotides. These "variants" are encompassed by this invention.

Preferably, the polynucleotide of the invention is an isolated polynucleotide. The term "isolated" polynucleotide refers to a polynucleotide that is substantially free from other nucleic acid sequences, such as and not limited to other chromosomal and extrachromosomal DNA and RNA. Isolated polynucleotides may be purified from a host cell. Conventional nucleic acid purification methods known to skilled artisans may be used to obtain isolated polynucleotides. The term also includes recombinant polynucleotides and chemically synthesized polynucleotides.

The invention further relates to a group of polynucleotides which together encode the modified VWF of the invention, or the polypeptide of the invention comprising the modified VWF. A first polynucleotide in the group may encode the N-terminal part of the modified VWF, and a second polynucleotide may encode the C-terminal part of the modified VWF.

Yet another aspect of the invention is a plasmid or vector comprising a polynucleotide according to the invention. Preferably, the plasmid or vector is an expression vector. In a particular embodiment, the vector is a transfer vector for use in human gene therapy.

The invention also relates to a group of plasmids or vectors that comprise the above group of polynucleotides. A first plasmid or vector may contain said first polynucleotide, and a second plasmid or vector may contain said second polynucleotide. Alternatively, both coding sequences are cloned into one expression vector either using two separate promoter sequences or one promoter and an internal ribosome entry site (IRES) element which may be used for example to direct the expression furin to enhance the generation of mature VWF.

Still another aspect of the invention is a host cell comprising a polynucleotide, a plasmid or vector of the invention, or a group of polynucleotides or a group of plasmids or vectors as described herein.

The host cells of the invention may be employed in a method of producing a modified VWF or a polypeptide comprising said modified VWF, which is part of this invention. The method comprises:
 (a) culturing host cells of the invention under conditions such that the desired modified protein is expressed; and
 (b) optionally recovering the desired modified protein from the host cells or from the culture medium.

It is preferred to purify the modified VWF of the present invention, or the polypeptide comprising the modified VWF to ≥80% purity, more preferably ≥95% purity, and particularly preferred is a pharmaceutically pure state that is greater than 99.9% pure with respect to contaminating macromolecules, particularly other proteins and nucleic acids, and free of infectious and pyrogenic agents. Preferably, an isolated or purified modified VWF of the invention or polypeptide of the invention is substantially free of other, non-related polypeptides.

The various products of the invention are useful as medicaments. Accordingly, the invention relates to a pharmaceutical composition comprising a modified VWF or a polypeptide comprising said modified VWF as described herein, a polynucleotide of the invention, or a plasmid or vector of the invention.

The invention also concerns a method of treating an individual suffering from a blood coagulation disorder such as hemophilia A or B or VWD. The method comprises administering to said individual an efficient amount of (i) FVIII and of the modified VWF or the polypeptide comprising the modified VWF or (ii) of the complex of FVIII with modified VWF or (iii) of the complex of FVIII with the polypeptide comprising modified VWF as described herein. In another embodiment, the method comprises administering to the individual an efficient amount of a polynucleotide of the invention or of a plasmid or vector of the invention. Alternatively, the method may comprise administering to the individual an efficient amount of the host cells of the invention described herein.

Expression of the Proposed Mutants

The production of recombinant mutant proteins at high levels in suitable host cells requires the assembly of the above-mentioned modified cDNAs into efficient transcriptional units together with suitable regulatory elements in a recombinant expression vector that can be propagated in various expression systems according to methods known to those skilled in the art. Efficient transcriptional regulatory elements could be derived from viruses having animal cells as their natural hosts or from the chromosomal DNA of animal cells. Preferably, promoter-enhancer combinations derived from the Simian Virus 40, adenovirus, BK polyoma virus, human cytomegalovirus, or the long terminal repeat of Rous sarcoma virus, or promoter-enhancer combinations including strongly constitutively transcribed genes in animal cells like beta-actin or GRP78 can be used. In order to achieve stable high levels of mRNA transcribed from the cDNAs, the transcriptional unit should contain in its 3'-proximal part a DNA region encoding a transcriptional termination-polyadenylation sequence. Preferably, this sequence is derived from the Simian Virus 40 early transcriptional region, the rabbit beta-globin gene, or the human tissue plasminogen activator gene.

The cDNAs are then integrated into the genome of a suitable host cell line for expression of the modified FVIII and/or VWF proteins. Preferably this cell line should be an animal cell-line of vertebrate origin in order to ensure correct folding, disulfide bond formation, asparagine-linked glycosylation and other post-translational modifications as well as secretion into the cultivation medium. Examples on other post-translational modifications are tyrosine 0-sulfation and proteolytic processing of the nascent polypeptide chain. Examples of cell lines that can be used are monkey COS-cells, mouse L-cells, mouse C127-cells, hamster BHK-21 cells, human embryonic kidney 293 cells, and hamster CHO-cells.

The recombinant expression vector encoding the corresponding cDNAs can be introduced into an animal cell line in several different ways. For instance, recombinant expression vectors can be created from vectors based on different animal viruses. Examples of these are vectors based on baculovirus, vaccinia virus, adenovirus, and preferably bovine papilloma virus.

The transcription units encoding the corresponding DNA's can also be introduced into animal cells together with another recombinant gene which may function as a dominant selectable marker in these cells in order to facilitate the isolation of specific cell clones which have integrated the recombinant DNA into their genome. Examples of this type of dominant selectable marker genes are Tn5 amino glycoside phosphotransferase, conferring resistance to gentamycin (G418), hygromycin phosphotransferase, conferring resistance to hygromycin, and puromycin acetyl transferase, conferring resistance to puromycin. The recombinant expression vector encoding such a selectable marker can reside either on the same vector as the one encoding the cDNA of the desired protein, or it can be encoded on a separate vector which is simultaneously introduced and integrated to the genome of the host cell, frequently resulting in a tight physical linkage between the different transcription units.

Other types of selectable marker genes which can be used together with the cDNA of the desired protein are based on various transcription units encoding dihydrofolate reductase (dhfr). After introduction of this type of gene into cells lacking endogenous dhfr-activity, preferentially CHO-cells (DUKX-B11, DG-44), it will enable these to grow in media lacking nucleosides. An example of such a medium is Ham's F12 without hypoxanthine, thymidine, and glycine. These dhfr-genes can be introduced together with the FVIII cDNA transcriptional units into CHO-cells of the above type, either linked on the same vector or on different vectors, thus creating dhfr-positive cell lines producing recombinant protein.

If the above cell lines are grown in the presence of the cytotoxic dhfr-inhibitor methotrexate, new cell lines resistant to methotrexate will emerge. These cell lines may produce recombinant protein at an increased rate due to the amplified number of linked dhfr and the desired protein's transcriptional units. When propagating these cell lines in increasing concentrations of methotrexate (1-10000 nM), new cell lines can be obtained which produce the desired protein at very high rate.

The above cell lines producing the desired protein can be grown on a large scale, either in suspension culture or on various solid supports. Examples of these supports are micro carriers based on dextran or collagen matrices, or solid supports in the form of hollow fibres or various ceramic materials. When grown in cell suspension culture or on micro carriers the culture of the above cell lines can be performed either as a bath culture or as a perfusion culture with continuous production of conditioned medium over extended periods of time. Thus, according to the present invention, the above cell lines are well suited for the development of an industrial process for the production of the desired recombinant mutant proteins Purification and Formulation The recombinant modified VWF protein, which accumulates in the medium of secreting cells of the above types, can be concentrated and purified by a variety of biochemical and chromatographic methods, including methods utilizing differences in size, charge, hydrophobicity, solubility, specific affinity, etc. between the desired protein and other substances in the cell cultivation medium.

An example of such purification is the adsorption of the recombinant mutant protein to a monoclonal antibody, directed to e.g. a HLEP, preferably human albumin, or directed to the respective coagulation factor, which is immobilised on a solid support. After adsorption of the modified VWF to the support, washing and desorption, the protein can be further purified by a variety of chromatographic techniques based on the above properties.

The order of the purification steps is chosen e.g. according to capacity and selectivity of the steps, stability of the support or other aspects. Preferred purification steps include but are not limited to ion exchange chromatography steps, immune affinity chromatography steps, affinity chromatography steps, hydrophobic interaction chromatography steps, dye chromatography steps, hydroxyapatite chromatography steps, multimodal chromatography steps, and size exclusion chromatography steps.

In order to minimize the theoretical risk of virus contaminations, additional steps may be included in the process that allow effective inactivation or elimination of viruses. Such steps e.g. are heat treatment in the liquid or solid state, treatment with solvents and/or detergents, radiation in the visible or UV spectrum, gamma-radiation or nanofiltration.

The modified polynucleotides (e.g. DNA) of this invention may also be integrated into a transfer vector for use in the human gene therapy.

The various embodiments described herein may be combined with each other. The present invention will be further described in more detail in the following examples thereof. This description of specific embodiments of the invention will be made in conjunction with the appended figures.

The modified VWF as described in this invention can be formulated into pharmaceutical preparations for therapeutic use. The purified protein may be dissolved in conventional physiologically compatible aqueous buffer solutions to which there may be added, optionally, pharmaceutical excipients to provide pharmaceutical preparations.

Such pharmaceutical carriers and excipients as well as suitable pharmaceutical formulations are well known in the art (see for example "Pharmaceutical Formulation Development of Peptides and Proteins", Frokjaer et al., Taylor & Francis (2000) or "Handbook of Pharmaceutical Excipients", 3rd edition, Kibbe et al., Pharmaceutical Press (2000)). Standard pharmaceutical formulation techniques are well known to persons skilled in the art (see, e.g., 2005 Physicians' Desk Reference®, Thomson Healthcare: Montvale, N.J., 2004; Remington: The Science and Practice of Pharmacy, 20th ed., Gennaro et al., Eds. Lippincott Williams & Wilkins: Philadelphia, Pa., 2000). In particular, the pharmaceutical composition comprising the polypeptide variant of the invention may be formulated in lyophilized or stable liquid form. The polypeptide variant may be lyophilized by a variety of procedures known in the art. Lyophilized formulations are reconstituted prior to use by the addition of one or more pharmaceutically acceptable diluents such as sterile water for injection or sterile physiological saline solution.

Formulations of the composition are delivered to the individual by any pharmaceutically suitable means of administration. Various delivery systems are known and can be used to administer the composition by any convenient route. Preferentially, the compositions of the invention are administered systemically. For systemic use, the proteins of the invention are formulated for parenteral (e.g. intravenous, subcutaneous, intramuscular, intraperitoneal, intracerebral, intrapulmonary, intranasal or transdermal) or enteral (e.g., oral, vaginal or rectal) delivery according to conventional methods. The most preferential routes of administration are intravenous and subcutaneous administration. The formulations can be administered continuously by infusion or by bolus injection. Some formulations encompass slow release systems.

The proteins of the present invention are administered to patients in a therapeutically effective dose, meaning a dose that is sufficient to produce the desired effects, preventing or lessening the severity or spread of the condition or indication being treated without reaching a dose which produces intolerable adverse side effects. The exact dose depends on many factors as e.g. the indication, formulation, and mode of administration and has to be determined in preclinical and clinical trials for each respective indication.

The pharmaceutical composition of the invention may be administered alone or in conjunction with other therapeutic agents. These agents may be incorporated as part of the same pharmaceutical. One example of such an agent is the combination of modified VWF with FVIII.

A summary of the sequences referred to herein is set out in Table 2.

TABLE 2

| SEQ ID NO: | Description |
|---|---|
| 1 | Nucleotide sequence of DNA encoding SEQ ID NO: 2 |
| 2 | Amino acid sequence of human VWF pre-propylpeptide |
| 3 | Amino acid sequence of D' domain of human VWF |
| 4 | Amino acid sequence of mature human VWF |
| 5 | S764G/S766Y |
| 6 | S764P/S766I |
| 7 | S764P/S766M |
| 8 | S764V/S766Y |
| 9 | S764E/S766Y |
| 10 | S764Y/S766Y |
| 11 | S764L/S766Y |
| 12 | S764P/S766W |
| 13 | S766W/S806A |
| 14 | S766Y/P769K |
| 15 | S766Y/P769N |
| 16 | S766Y/P769R |
| 17 | S764P/S766L |
| 18 | Amino acid sequence of human Factor VIII |
| 19 | Amino acid sequence of a mature single-chain Factor VIII |
| 20 | Amino acid sequence of human serum albumin |

EXAMPLES

Example 1 vWF Point Mutants with Improved FVIII Binding

Background

As discussed above the majority of circulating FVIII is in complex with VWF. In humans, FVIII is cleared from the blood with a $t_{1/2}$ of approximately 2 hr and 16 hr in the absence and presence of VWF, respectively. Although VWF imparts an increase in FVIII half-life, it also places an upper limit on the $t_{1/2}$ that is dictated by its own half-life. U.S. Pat. No. 8,575,104 discloses a VWF-albumin fusion protein. This fusion protein has a five-fold longer half-life than wild type VWF in a rodent model. A stable complex between this fusion protein and FVIII may confer additional half-life benefits for FVIII. Although the equilibrium binding constant for the FVIII/vWF interaction is high, the binding kinetics are rapid and any FVIII in complex with the VWF-albumin fusion protein will quickly exchange with endogenous vWF upon infusion. Accordingly if the off-rate of FVIII with VWF-albumin fusion is substantially equivalent to the off-rate of FVIII with native VWF then the use of the VWF-albumin fusion will not provide any substantial increase in the half life of FVIII.

Accordingly, in order to take advantage of the longer half life of the VWF-albumin fusion to extend the half life of FVIII it is necessary to decrease the off-rate of FVIII with the VWF-albumin fusion. From modeling studies taking advantage of measurement made in patients with Type 2N von Willebrand disease in which the level of VWF is normal but the ability of the VWF to associate with FVIII is severely diminished it has been estimated that at least a five fold decrease in off-rate is required to provide a clinically relevant improvement in FVIII half life. The postulated relationship between decrease in FVIII VWF-albumin fusion off-rate and increase in FVIII half life is set out in Table 3.

TABLE 3

| Decrease in FVIII VWF-albumin fusion off-rate | Postulated increase in FVIII half life (For 50 IU/kg of FVIII and 100 IU/kg of VWF with the VWF 5x half life extended) |
|---|---|
| 2 fold | 2.2 |
| 3 fold | 2.6 |
| 5 fold | 3 |
| 10 fold | 3.6 |
| 20 fold | 4.1 |

TABLE 3-continued

In an effort to decrease FVIII VWF-albumin fusion off-rate experiments were conducted to assess whether mutant VWF-albumin fusion protein may provide a significantly slower FVIII off-rate thereby providing a viable option to extend the half-life of FVIII through stable association with the VWF-albumin fusion protein.

A series of mutants were constructed around amino acid positions 764, 765, 766, 768, 769, 773, 806 and 809 of vWF with the intention of slowing the rate of dissociation of bound FVIII. In these experiments a recombinant form of FVIII was used. This FVIII is described in Zollner et al 2013, Thrombosis Research, 132:280-287. Initially, FVIII binding was measured for vWF constructs that had one of the above mentioned residues mutated to all genetic encoded amino acids, excluding cysteine. Following identification of improved binders additional sets of variants were produced including combinations of mutations. In addition, as the half life extension provided by the albumin fusion is dependent on FcRn-mediated recycling a number of the mutants were also tested at a pH 5.5. The results for the various mutations are shown in Tables 4 to 19.

Methods

A synthetic, codon-optimised cDNA encoding the D' and D3 domains of human von Willebrand Factor (vWF; amino acids (aa) 764-1270; based on GenBank accession no. NP_000543 and the domain boundaries elucidated by Zhou et al 2012 Blood 120: 449-458) was obtained from GeneART AG (Regensberg, Germany). This was modified at the 5' end to encode its own signal peptide (aa1-22) and at the 3' end to encode a C-terminal 8×His-tag. The construct (Hu-vWF[764-1270]-8His) was directionally cloned into the pcDNA3.1 mammalian expression vector (Invitrogen, USA) with a Kozak consensus sequence (GCCACC) upstream of the initiating methionine and a double stop codon (TGA) at the 3' end of the open reading frame, and the plasmid sequence confirmed by automated sequencing. This expression plasmid was then used as a template to make single, double or triple residue changes at Ser764, Leu765, Ser766 or Lys773 using standard PCR techniques and the constructs cloned into pcDNA3.1 and sequenced as described above. A second codon-optimised cDNA encoding the D1 and D2 domains (aa1-762) of Hu-vWF with a C-terminal FLAG tag (DYKDDDDK) was also synthesized and obtained from GeneArt; this was cloned as above into pcDNA3.1 and sequenced.

For transient mammalian expression, Freestyle™ 293 suspension cells (Invitrogen] were grown to $1.1 \times 10^6$ cells/ml in 5 ml Freestyle Expression media (Invitrogen). 7 µL 293Fectin (Invitrogen) transfection reagent was pre-incubated for 5 minutes with 167 µL Opti-MEM I medium (Invitrogen), then added to 2.5 µg plasmid DNA encoding wild-type/mutant Hu-vWF[764-1270]-8His plus 2.5 µg plasmid DNA encoding Hu-vWF[1-762]-FLAG and the mixture incubated for a further 20 minutes. The DNA-293Fectin complex was added to the cells which were cultured for 6 days at 37° C., 8% $CO_2$ in a shaking incubator at 250 rpm. Culture supernatants were harvested by centrifugation at 2000 rpm for 5 minutes and stored at 4° C. for analysis.

Binding kinetics were investigated by surface plasmon resonance using a Biacore 4000 biosensor at 37° C. Each mutant was captured from cell culture medium to a density of 40-150RU on a CM-5 sensor chip pre-immobilised with anti-His antibody (14,000 RU). In an initial screening study, FVIII was injected over the captured mutants for 5 minutes at 1 nM and dissociation monitored for 5 minutes. Mutants that showed a decrease in kd relative to wild-type were then re-examined with FVIII injected for 5 minutes at 1, 0.5 and 0.25 nM, and dissociation monitored for 30 minutes.

All sensorgrams were double referenced by subtraction of signals from a reference spot (containing only immobilised anti His antibody) and from a blank injection. Binding kinetics were determined by fitting the double referenced sensorgrams to a 1:1 kinetic model.

Results

Mutagenesis of serine 764 to proline generated a vWF variant with an approximately 3.5 fold decrease in off-rate and a 4.4 fold increase in affinity. Mutations at position 765 did not yield any better binders vis-a-vis wild type vWF. Numerous mutations at position 766 generated variant vWF molecules with improved off-rate characteristics and higher affinity than wild-type vWF (His, Arg, Val, Tyr, Trp, Thr, Phe, Be, Gln, Gly & Asn). Given that proline at position 764 conferred significant enhancement to off-rate while numerous mutations at position 766 positively impacted binding, a series of mutants were generated that consisted of S764P and all other genetic encoded amino acids, excluding cysteine, at position 766. Similar mutations were produced that contained S764P and all other genetic encoded amino acids, excluding cysteine, at position 765. A number of these double mutants have significantly slower off-rates and higher affinity vis-a-vis wild type vWF. In particular S764P in combination with S766I generates a vWF variant with a 22 fold decrease in off-rate and a 30 fold increase in affinity.

Example 2

Human Serum Albumin vWF Fusions with Point Mutants and FVIII Binding

Mouse anti-HSA antibody was immobilized on a CM5 chip using standard NHS/EDC coupling chemistry. Typically, the immobilization level was between 10,000 and 12,000 RU. Each batch of vWF-HSA (monomers and dimers) was captured on a single spot in each flow cell for 2 minutes at various concentrations ranging from 0.1-1 µg/ml. Capture levels ranged from 40-150RU. An adjacent spot in which anti-vWF was immobilized, but no vWF-HSA captured was used as a reference. Capture was performed every cycle, before FVIII binding analysis.

FVIII was injected at random and in duplicate over all spots in all flow cells at varying concentrations depending on the affinity of the interaction and the pH of the analysis. The association and dissociation of FVIII was monitored for various time frames that best suited the interaction taking place.

Post the dissociation period the surface was regenerated with a 30 second injection of 25 mM Glycine pH2.6. Running buffer throughout was 10 mM HEPES, 150 mM NaCl, 10 mM Na Citrate, 2.5 mM $CaCl_2$, 0.1% BSA, pH7.3 and pH5, while the flow rate was 30 µl/min. Each interaction was measured 4 times (n=4) at 37° C.

Responses for binding to the reference spot were subtracted from those of the vWF-HSA captured spots. Responses from blank injections were then subtracted from those of all other samples to produce double-referenced sensorgrams. Double referenced sensorgrams were fitted to a 1:1 kinetic model, including a term for mass transport limitation. Association and dissociation rates were fitted globally and Rmax fitted locally. The results obtained are set out in Tables 20 and 21.

TABLE 4

S764X mutants were X is one of the remaining genetic encoded amino acids, excluding cysteine.

| Mutant | ka (1/Ms) | kd (1/s) | KD (M) |
|---|---|---|---|
| S764P | 9.07E+06 | 3.25E−04 | 3.58E−11 |
| S764Y | 8.07E+06 | 8.87E−04 | 1.10E−10 |
| S764E | 6.38E+06 | 7.43E−04 | 1.16E−10 |
| S764L | 8.47E+06 | 9.95E−04 | 1.18E−10 |
| S764A | 6.85E+06 | 8.08E−04 | 1.18E−10 |
| S764G | 6.82E+06 | 8.18E−04 | 1.20E−10 |
| S764I | 9.02E+06 | 1.27E−03 | 1.41E−10 |
| S764W | 9.46E+06 | 1.41E−03 | 1.49E−10 |
| wt | 7.33E+06 | 1.15E−03 | 1.57E−10 |
| wt | 7.43E+06 | 1.18E−03 | 1.59E−10 |
| S76R | 1.06E+07 | 1.77E−03 | 1.67E−10 |
| S764F | 8.14E+06 | 1.40E−03 | 1.72E−10 |
| S764N | 6.21E+06 | 1.26E−03 | 2.03E−10 |
| S764M | 8.94E+06 | 1.90E−03 | 2.12E−10 |
| S764V | 7.30E+06 | 1.69E−03 | 2.32E−10 |
| S764T | 7.17E+06 | 1.89E−03 | 2.64E−10 |
| S764D | 6.27E+06 | 1.68E−03 | 2.68E−10 |
| S76H | 8.96E+06 | 2.78E−03 | 3.10E−10 |
| S76K | 1.59E+07 | 5.09E−03 | 3.19E−10 |
| S764Q | 2.97E+06 | 2.04E−03 | 6.86E−10 |

TABLE 5

L765X mutants were X is one of the remaining genetic encoded amino acids, excluding cysteine.

| Mutant | ka (1/Ms) | kd (1/s) | KD (M) |
|---|---|---|---|
| WT-L765A | 3.40E+07 | 7.88E−03 | 2.32E−10 |
| WT-L765N | N/D | | |
| WT-L765Q | N/D | | |
| WT-L765G | N/D | | |
| WT-L765I | 6.01E+06 | 1.16E−03 | 1.92E−10 |
| WT-L765M | 6.81E+06 | 1.95E−03 | 2.87E−10 |
| WT-L765F | 8.91E+06 | 1.74E−03 | 1.96E−10 |
| WT-L765P | 1.13E+08 | 4.80E−02 | 4.25E−10 |
| WT-L765S | 3.46E+07 | 9.13E−03 | 2.64E−10 |
| WT-L765T | 7.53E+07 | 1.75E−02 | 2.32E−10 |
| WT-L765W | 3.53E+07 | 1.42E−02 | 4.03E−10 |
| WT-L765Y | 8.44E+07 | 4.36E−02 | 5.17E−10 |
| WT-L765V | 6.24E+06 | 4.76E−03 | 7.63E−10 |
| WT-L765D | N/D | | |
| WT-L765E | N/D | | |
| WT-L765R | 1.32E+08 | 1.55E−02 | 1.17E−10 |
| WT-L765H | N/D | | |
| WT-L765K | N/D | | |
| WT | 7.33E+06 | 1.15E−03 | 1.57E−10 |

N/D: weak binding, poor fit, fast off rate

TABLE 6

S766X mutants were X is one of the remaining genetic encoded amino acids, excluding cysteine.

| Mutant | ka (1/Ms) | kd (1/s) | KD (M) |
|---|---|---|---|
| WT-S766A | 7.47E+06 | 1.54E−03 | 2.06E−10 |
| WT-S766N | 8.71E+06 | 8.80E−04 | 1.01E−10 |
| WT-S766Q | 7.42E+06 | 5.16E−04 | 6.94E−11 |
| WT-S766G | 9.34E+06 | 1.88E−03 | 2.01E−10 |
| WT-S766I | 6.17E+06 | 7.93E−04 | 1.29E−10 |

TABLE 6-continued

S766X mutants were X is one of the remaining genetic encoded amino acids, excluding cysteine.

| Mutant | ka (1/Ms) | kd (1/s) | KD (M) |
|---|---|---|---|
| WT-S766L | 7.31E+06 | 1.21E−03 | 1.65E−10 |
| WT-S766M | N/D | | |
| WT-S766F | 7.46E+06 | 2.74E−04 | 3.67E−11 |
| WT-S766P | 1.16E+07 | 3.45E−03 | 2.98E−10 |
| WT-S766T | 7.12E+06 | 4.98E−04 | 7.00E−11 |
| WT-S766W | 6.62E+06 | 2.03E−04 | 3.07E−11 |
| WT-S766Y | 6.98E+06 | 1.95E−04 | 2.79E−11 |
| WT-S766V | 6.01E+06 | 2.60E−04 | 4.33E−11 |
| WT-S766D | N/D | | |
| WT-S766E | 2.53E+07 | 1.89E−03 | 7.48E−11 |
| WT-S766R | 9.04E+06 | 3.63E−04 | 4.02E−11 |
| WT-S766H | 7.19E+06 | 3.06E−04 | 4.25E−11 |
| WT-S766K | 1.02E+07 | 3.22E−03 | 3.14E−10 |
| WT | 7.33E+06 | 1.15E−03 | 1.57E−10 |

N/D: weak binding, poor fit, fast off-rate

TABLE 7

| Mutant | Ka (1/Ms) | kd (1/s) | KD (M) |
|---|---|---|---|
| WT-K773T | 1.42E+07 | 6.97E−04 | 4.92E−11 |
| WT-K773A | 5.81E+06 | 8.83E−04 | 1.52E−10 |
| WT-K773L | 1.88E+07 | 1.10E−03 | 5.86E−11 |
| WT-K773R | 1.45E+07 | 1.23E−03 | 8.46E−11 |
| WT-K773Q | 8.60E+06 | 1.45E−03 | 1.68E−10 |
| WT-K773M | 1.57E+07 | 2.35E−03 | 1.50E−10 |
| WT-K773S | 1.35E+07 | 3.23E−03 | 2.40E−10 |
| WT-K773P | 9.58E+06 | 3.33E−03 | 3.48E−10 |
| WT-K773I | 7.66E+07 | 4.09E−03 | 5.35E−11 |
| WT-K773V | 5.39E+07 | 5.23E−03 | 9.70E−11 |
| WT-K773H | 1.19E+09 | 1.57E−01 | 1.32E−10 |
| WT-K773N | 3.61E+09 | 8.36E−01 | 2.32E−10 |
| WT-K773W | N/D | | |
| WT-K773E | N/D | | |
| WT-K773D | N/D | | |
| WT-K773G | N/D | | |
| WT-K773F | N/D | | |
| WT-K773Y | N/D | | |
| WT | 7.33E+06 | 1.15E−03 | 1.57E−10 |

N/D: Binding was present, but accurate kinetic parameters could not be determined

TABLE 8

S764P, L765X mutants were X is one of the remaining genetic encoded amino acids, excluding cysteine.

| Mutant | ka (1/Ms) | kd (1/s) | KD (M) |
|---|---|---|---|
| S764P-L765A | 3.07E+07 | 2.78E−02 | 9.06E−10 |
| S764P-L765N | N/D | | |
| S764P-L765Q | 8.12E+06 | 7.14E−03 | 8.80E−10 |
| S764P-L765G | N/D | | |
| S764P-L765I | 8.08E+06 | 9.52E−05 | 1.18E−11 |
| S764P-L765M | 9.76E+06 | 2.37E−04 | 2.43E−11 |
| S764P-L765F | 1.69E+07 | 6.32E−04 | 3.73E−11 |
| S764P-L765P | 1.02E+07 | 2.42E−04 | 2.38E−11 |
| S764P-L765S | N/D | | |
| S764P-L765T | 1.39E+07 | 8.82E−03 | 6.34E−10 |
| S764P-L765W | 7.97E+06 | 5.14E−03 | 6.45E−10 |
| S764P-L765Y | 6.19E+06 | 2.20E−03 | 3.55E−10 |
| S764P-L765V | 6.19E+06 | 2.20E−03 | 3.55E−10 |
| S764P-L765D | N/D | | |
| S764P-L765E | N/D | | |
| S764P-L765R | N/D | | |
| S764P-L765H | 1.16E+07 | 6.42E−03 | 5.55E−10 |
| S764P-L765K | N/D | | |
| WT | 7.33E+06 | 1.15E−03 | 1.57E−10 |

N/D: weak binding, poor fit, fast off-rate

TABLE 9

S764P, S766X mutants were X is one of the remaining genetic encoded amino acids, excluding cysteine.

| Mutant | ka (1/Ms) | kd (1/s) | KD (M) |
|---|---|---|---|
| S764P-S766A | 1.35E+07 | 1.66E−04 | 1.23E−11 |
| S764P-S766N | 8.82E+06 | 9.14E−05 | 1.04E−11 |
| S764P-S766Q | 1.20E+07 | 1.23E−04 | 1.02E−11 |
| S764P-S766G | 1.79E+07 | 3.88E−04 | 2.17E−11 |
| S764P-S766I | 9.84E+06 | 5.14E−05 | 5.23E−12 |
| S764P-S766L | 1.44E+07 | 8.74E−05 | 6.06E−12 |
| S764P-S766M | 1.18E+07 | 5.76E−05 | 4.88E−12 |
| S764P-S766F | 1.35E+07 | 1.00E−04 | 7.41E−12 |
| S764P-S766P | 2.56E+07 | 2.17E−03 | 8.48E−11 |
| S764P-S766T | 9.01E+06 | 1.05E−04 | 1.16E−11 |
| S764P-S766W | 1.10E+07 | 8.00E−05 | 7.27E−12 |
| S764P-S766Y | 1.08E+07 | 7.71E−05 | 7.16E−12 |
| S764P-S766V | 8.19E+05 | 7.82E−05 | 9.56E−11 |
| S764P-S766D | 9.41E+06 | 1.20E−04 | 1.27E−11 |
| S764P-S766E | 8.04E+06 | 1.28E−04 | 1.60E−11 |
| S764P-S766R | 1.29E+07 | 1.19E−04 | 9.21E−12 |
| S764P-S766H | 1.40E+07 | 9.47E−05 | 6.76E−12 |
| S764P-S766K | 2.15E+07 | 3.01E−04 | 1.40E−11 |
| WT | 7.33E+06 | 1.15E−03 | 1.57E−10 |

N/D: weak binding, poor fit, fast off-rate

TABLE 10

| Mutant | ka (1/Ms) | kd (1/s) | KD (M) |
|---|---|---|---|
| S764P-K773R | 6.39E+06 | 7.42E−05 | 1.16E−11 |
| S764P-K773T | 4.68E+06 | 7.50E−05 | 1.60E−11 |
| S764P-K773Q | 4.44E+06 | 1.28E−04 | 2.88E−11 |
| S764P-K773V | 1.55E+07 | 1.57E−04 | 1.01E−11 |
| S764P-K773I | 1.79E+07 | 1.69E−04 | 9.43E−12 |
| S764P-K773M | 1.58E+07 | 1.70E−04 | 1.08E−11 |
| S764P-K773A | 6.37E+06 | 1.89E−04 | 2.97E−11 |
| S764P-K773S | 2.16E+07 | 3.06E−04 | 1.42E−11 |
| S764P-K773N | 5.50E+06 | 3.47E−04 | 6.31E−11 |
| S764P-K773P | 2.26E+07 | 5.01E−04 | 2.22E−11 |
| S764P-K773L | 4.60E+05 | 5.72E−04 | 1.24E−09 |
| S764P-K773H | 1.65E+07 | 6.36E−04 | 3.86E−11 |
| S764P-K773G | 1.75E+07 | 7.62E−04 | 4.36E−11 |
| S764P-K773F | 1.02E+07 | 1.23E−03 | 1.21E−10 |
| S764P-K773Y | 1.63E+07 | 1.36E−03 | 8.35E−11 |
| S764P-K773D | 1.77E+07 | 2.40E−03 | 1.36E−10 |
| S764P-K773W | 1.25E+07 | 3.21E−03 | 2.57E−10 |
| S764P-K773E | 6.73E+07 | 5.15E−03 | 7.65E−11 |
| WT | 7.33E+06 | 1.15E−03 | 1.57E−10 |

TABLE 11

| Mutant | ka (1/Ms) | kd (1/s) | KD (M) |
|---|---|---|---|
| S766Y-K773T | 1.20E+07 | 2.69E−04 | 2.24E−11 |
| S766Y-K773L | 1.79E+07 | 3.45E−04 | 1.92E−11 |
| S766Y-K773R | 1.40E+07 | 4.69E−04 | 3.35E−11 |
| S766Y-K773I | 8.02E+06 | 5.69E−04 | 7.10E−11 |
| S766Y-K773M | 1.97E+07 | 6.59E−04 | 3.35E−11 |
| S766Y-K773V | 1.74E+07 | 8.61E−04 | 4.94E−11 |
| S766Y-K773Q | 2.39E+07 | 9.39E−04 | 3.93E−11 |
| S766Y-K773A | 1.88E+07 | 1.22E−03 | 6.51E−11 |
| S766Y-K773S | 1.75E+07 | 1.38E−03 | 7.85E−11 |
| S766Y-K773G | 6.02E+07 | 1.97E−03 | 3.27E−11 |
| S766Y-K773P | 2.16E+07 | 2.43E−03 | 1.12E−10 |
| S766Y-K773F | 2.05E+07 | 3.24E−03 | 1.58E−10 |
| S766Y-K773W | 2.93E+07 | 3.93E−03 | 1.34E−10 |
| S766Y-K773Y | 2.24E+07 | 4.04E−03 | 1.80E−10 |
| S766Y-K773E | 1.84E+07 | 4.81E−03 | 2.61E−10 |
| S766Y-K773N | 5.15E+07 | 5.07E−03 | 9.84E−11 |
| S766Y-K773H | 5.47E+07 | 6.20E−03 | 1.14E−10 |
| S766Y-K773D | 1.25E+08 | 4.27E−02 | 3.43E−10 |
| WT | 7.33E+06 | 1.15E−03 | 1.57E−10 |

TABLE 12

| Mutant | ka (1/Ms) | kd (1/s) | KD (M) |
| --- | --- | --- | --- |
| S764G/S766Y | 1.37E+07 | 2.69E-05 | 1.96E-12 |
| S764V/S766Y | 2.99E+07 | 6.41E-05 | 2.15E-12 |
| S764A/S766Y | 2.98E+07 | 7.21E-05 | 2.42E-12 |
| S764E/S766Y | 1.97E+07 | 7.64E-05 | 3.87E-12 |
| S764P/S766Y | 1.08E+07 | 7.71E-05 | 7.16E-12 |
| S764Y/S766Y | 3.19E+07 | 7.88E-05 | 2.47E-12 |
| S764L/S766Y | 3.52E+07 | 7.99E-05 | 2.27E-12 |
| S764N/S766Y | 1.28E+07 | 8.88E-05 | 6.92E-12 |
| S764R/S766Y | 3.23E+07 | 9.20E-05 | 2.85E-12 |
| S764F/S766Y | 7.68E+06 | 9.36E-05 | 1.22E-11 |
| S764I/S766Y | 1.03E+07 | 9.52E-05 | 9.23E-12 |
| S764W/S766Y | 8.88E+06 | 9.67E-05 | 1.09E-11 |
| S764M/S766Y | 7.15E+06 | 1.03E-04 | 1.44E-11 |
| S764Q/S766Y | 1.19E+07 | 1.09E-04 | 9.18E-12 |
| S764D/S766Y | 3.78E+07 | 1.18E-04 | 3.12E-12 |
| S764T/S766Y | 2.58E+07 | 1.36E-04 | 5.27E-12 |
| S764H/S766Y | 4.56E+07 | 2.92E-04 | 6.39E-12 |
| S764K/S766Y | 1.89E+07 | 8.22E-04 | 4.35E-11 |
| WT | 7.33E+06 | 1.15E-03 | 1.57E-10 |

TABLE 13

| Mutant | ka (1/Ms) | kd (1/s) | KD (M) |
| --- | --- | --- | --- |
| S764P-L765H-S766I | 1.56E+06 | 6.60E-05 | 4.24E-11 |
| S764P-L765V-S766I | 5.62E+07 | 1.16E-04 | 2.07E-12 |
| S764P-L765M-S766I | 5.69E+07 | 1.37E-04 | 2.41E-12 |
| S764P-L765W-S766I | 1.11E+06 | 1.46E-04 | 1.32E-10 |
| S764P-L765Q-S766I | 1.15E+06 | 2.86E-04 | 2.48E-10 |
| S764P-L765K-S766I | 6.88E+07 | 1.50E-03 | 2.18E-11 |
| S764P-L765Y-S766I | 5.17E+07 | 1.90E-03 | 3.67E-11 |
| S764P-L765T-S766I | 1.15E+08 | 3.31E-03 | 2.87E-11 |
| S764P-L765I-S766I | 6.34E+06 | 1.03E-02 | 1.62E-09 |
| S764P-L765G-S766I | 5.04E+07 | 1.22E-02 | 2.41E-10 |
| S764P-L765R-S766I | 7.96E+07 | 1.73E-02 | 2.18E-10 |
| S764P-L765E-S766I | 1.03E+06 | 5.50E-02 | 5.36E-08 |
| S764P-L765F-S766I | N/D | | |
| S764P-L765N-S766I | N/D | | |
| S764P-L765D-S766I | N/D | | |
| S764P-L765P-S766I | N/D | | |
| S764P-L765S-S766I | N/D | | |
| S764P-L765A-S766I | N/D | | |

N/D: Binding was present, but accurate kinetic parameters could not be determined

TABLE 14

| Mutant | ka (1/Ms) | kd (1/s) | KD (M) |
| --- | --- | --- | --- |
| dupS764/S764P/S766I | 6.23E+06 | 1.59E-03 | 2.55E-10 |
| dupS764/S764P/S766I | 1.25E+07 | 2.50E-03 | 1.99E-10 |
| dS764-dL765-S766I | | | |
| dS764-dL765-S766Y | N/D | | |
| delS764-S766Y | 6.20E+06 | 2.07E-04 | 3.34E-11 |
| delS764-S766W | 6.60E+06 | 3.15E-04 | 4.78E-11 |
| delS764-S766L | 6.21E+06 | 5.85E-04 | 9.42E-11 |
| delS764-S766M | 7.25E+06 | 7.26E-04 | 1.00E-10 |
| delS764-S766I | 7.09E+06 | 8.27E-04 | 1.17E-10 |
| delS764-S766S | 7.30E+06 | 8.46E-04 | 1.16E-10 |

N/D: Binding was present, but accurate kinetic parameters could not be determined

TABLE 15

PH 5.5

| Mutant | ka (1/Ms) | kd (1/s) | KD (M) |
| --- | --- | --- | --- |
| S764P-S766W | 2.77E+05 | 4.75E-05 | 1.72E-10 |
| S764P-S766M | 3.14E+05 | 9.16E-05 | 2.92E-10 |
| S764P-S766L | 4.45E+05 | 1.04E-04 | 2.34E-10 |
| WT | 2.03E+06 | 3.88E-02 | 1.91E-08 |
| S764P-S766I | N/D | | |

TABLE 15-continued

PH 5.5

| Mutant | ka (1/Ms) | kd (1/s) | KD (M) |
| --- | --- | --- | --- |
| S764P-S766Y | N/D | | |
| S764P-S766H | N/D | | |

N/D: Binding was present, but accurate kinetic parameters could not be determined

TABLE 16

S766W, L809X mutants were X is one of the remaining genetic encoded amino acids, excluding cysteine

| Mutant | ka (1/Ms) | kd (1/s) | KD (M) |
| --- | --- | --- | --- |
| S766W-L809A | 4.45E+06 | 1.15E-03 | 2.58E-10 |
| S766W-L809D | 4.46E+06 | 1.90E-03 | 4.25E-10 |
| S766W-L809E | 5.84E+06 | 1.55E-03 | 2.65E-10 |
| S766W-L809F | 3.26E+06 | 7.44E-04 | 2.28E-10 |
| S766W-L809G | 6.21E+06 | 2.26E-03 | 3.63E-10 |
| S766W-L809H | 2.87E+06 | 1.14E-03 | 3.97E-10 |
| S766W-L809I | 5.23E+06 | 5.41E-04 | 1.03E-10 |
| S766W-L809K | 7.00E+06 | 1.53E-03 | 2.19E-10 |
| S766W-L809M | 4.99E+06 | 5.81E-04 | 1.17E-10 |
| S766W-L809N | 6.15E+06 | 2.27E-03 | 3.69E-10 |
| S766W-L809P | NB | NB | NB |
| S766W-L809Q | 5.33E+06 | 1.13E-03 | 2.12E-10 |
| S766W-L809R | 6.07E+06 | 2.13E-03 | 3.52E-10 |
| S766W-L809S | 6.54E+06 | 1.44E-03 | 2.20E-10 |
| S766W-L809T | 8.72E+06 | 1.41E-03 | 1.61E-10 |
| S766W-L809V | 7.70E+06 | 9.40E-04 | 1.22E-10 |
| S766W-L809W | 4.81E+06 | 3.12E-03 | 6.48E-10 |
| S766W-L809Y | 6.77E+06 | 3.39E-03 | 5.00E-10 |
| vWF WT | 4.98E+06 | 8.86E-04 | 1.78E-10 |

TABLE 17

S766W, S806X mutants were X is one of the remaining genetic encoded amino acids, excluding cysteine

| Mutant | ka (1/Ms) | kd (1/s) | KD (M) |
| --- | --- | --- | --- |
| S766W-S806A | 4.84E+06 | 3.76E-04 | 7.78E-11 |
| S766W-S806D | 4.20E+06 | 6.88E-04 | 1.64E-10 |
| S766W-S806E | 5.93E+06 | 1.29E-03 | 2.17E-10 |
| S766W-S806F | NB | NB | NB |
| S766W-S806G | 5.46E+06 | 1.34E-03 | 2.45E-10 |
| S766W-S806H | 8.90E+06 | 8.28E-04 | 9.30E-11 |
| S766W-S806I | 1.58E+06 | 4.47E-04 | 2.83E-10 |
| S766W-S806K | N/D | | |
| S766W-S806L | NB | NB | NB |
| S766W-S806M | 2.05E+06 | 8.72E-04 | 4.25E-10 |
| S766W-S806N | 3.84E+06 | 5.85E-04 | 1.52E-10 |
| S766W-S806P | 4.26E+06 | 5.66E-04 | 1.33E-10 |
| S766W-S806Q | 4.33E+06 | 1.76E-03 | 4.07E-10 |
| S766W-S806R | 8.28E+06 | 1.07E-02 | 1.29E-09 |
| S766W-S806T | 5.25E+06 | 6.54E-04 | 1.25E-10 |
| S766W-S806V | 4.17E+06 | 6.19E-04 | 1.49E-10 |
| S766W-S806W | NB | NB | NB |
| S766W-S806Y | NB | NB | NB |
| vWF WT | 4.98E+06 | 8.86E-04 | 1.78E-10 |

N/D: Binding was present, but accurate kinetic parameters could not be determined

TABLE 18

S766Y, P769X mutants were X is one of the remaining genetic encoded amino acids, excluding cysteine

| Mutant | ka (1/Ms) | kd (1/s) | KD (M) |
| --- | --- | --- | --- |
| S766Y-P769A | 4.90E+06 | 5.19E-04 | 1.06E-10 |
| S766Y-P769D | 4.63E+06 | 7.63E-04 | 1.65E-10 |
| S766Y-P769E | 4.42E+06 | 4.14E-04 | 9.36E-11 |

TABLE 18-continued

S766Y, P769X mutants were X is one of the remaining genetic encoded amino acids, excluding cysteine

| Mutant | ka (1/Ms) | kd (1/s) | KD (M) |
|---|---|---|---|
| S766Y-P769F | 5.54E+06 | 4.27E−04 | 7.72E−11 |
| S766Y-P769G | 3.70E+06 | 7.83E−04 | 2.12E−10 |
| S766Y-P769H | 5.16E+06 | 4.17E−04 | 8.09E−11 |
| S766Y-P769I | NB | NB | NB |
| S766Y-P769K | 6.31E+06 | 3.83E−04 | 6.07E−11 |
| S766Y-P769L | 6.44E+06 | 5.90E−04 | 9.17E−11 |
| S766Y-P769M | 4.75E+06 | 5.11E−04 | 1.08E−10 |
| S766Y-P769N | 1.60E+07 | 5.20E−04 | 3.25E−11 |
| S766Y-P769Q | NB | NB | NB |
| S766Y-P769R | 6.55E+06 | 2.95E−04 | 4.50E−11 |
| S766Y-P769S | 4.51E+06 | 5.11E−04 | 1.13E−10 |
| S766Y-P769T | 5.11E+06 | 5.00E−04 | 9.79E−11 |
| S766Y-P769V | 6.65E+06 | 5.65E−04 | 8.49E−11 |
| S766Y-P769W | 4.77E+06 | 4.21E−04 | 8.82E−11 |
| S766Y-P769Y | 4.68E+06 | 3.96E−04 | 8.47E−11 |
| vWF WT | 4.98E+06 | 8.86E−04 | 1.78E−10 |

TABLE 19

S766Y, R768X mutants were X is one of the remaining genetic encoded amino acids, excluding cysteine

| Mutant | ka (1/Ms) | kd (1/s) | KD (M) |
|---|---|---|---|
| S766Y-R768A | 6.99E+06 | 1.48E−03 | 2.12E−10 |
| S766Y-R768D | 4.94E+06 | 4.48E−03 | 9.08E−10 |
| S766Y-R768E | 5.65E+06 | 3.22E−03 | 5.69E−10 |
| S766Y-R768F | 6.51E+06 | 1.82E−03 | 2.79E−10 |
| S766Y-R768G | 3.20E+06 | 1.02E−03 | 3.20E−10 |
| S766Y-R768H | 4.02E+06 | 6.90E−04 | 1.72E−10 |
| S766Y-R768I | 5.03E+06 | 8.99E−04 | 1.79E−10 |
| S766Y-R768K | 3.83E+06 | 4.17E−04 | 1.09E−10 |
| S766Y-R768L | 4.24E+06 | 5.48E−04 | 1.29E−10 |
| S766Y-R768M | 4.08E+06 | 8.01E−04 | 1.96E−10 |
| S766Y-R768N | 4.18E+06 | 7.98E−04 | 1.91E−10 |
| S766Y-R768P | 6.71E+06 | 1.43E−03 | 2.13E−10 |
| S766Y-R768Q | 3.48E+06 | 6.06E−04 | 1.74E−10 |
| S766Y-R768S | 5.33E+06 | 1.29E−03 | 2.43E−10 |
| S766Y-R768T | 5.59E+06 | 1.43E−03 | 2.56E−10 |
| S766Y-R768V | 4.51E+06 | 9.18E−04 | 2.03E−10 |
| S766Y-R768W | 4.42E+06 | 9.40E−04 | 2.13E−10 |
| S766Y-R768Y | 6.74E+06 | 1.87E−03 | 2.77E−10 |
| vWF WT | 4.98E+06 | 8.86E−04 | 1.78E−10 |

TABLE 20

Dimers Binding to FVIII (pH 7.3)

| Mutant | ka (1/Ms) | kd (1/s) | KD (M) |
|---|---|---|---|
| S764P-S766I | 1.01E+07 (±3.41E6) | 5.00E−05 (±3.37E−6) | 3.96E−12 (±2.6E−13) |
| S764P-S766W | 1.24E+07 (±7.28E5) | 6.21E−05 (±2.52E−6) | 4.96E−12 (±1.9E−13) |
| S766Y | 1.03E+07 (±3.01E6) | 2.36E−04 (±4.27E−5) | 2.51E−11 (±3.83E−12) |
| S764E-S766Y | 7.75E+06 (±1.71E6) | 2.36E−04 (±2.90E−5) | 3.25E−11 (±4.57E−12) |
| S764I-S766W | 7.54E+06 (±5.15E5) | 2.41E−04 (±5.05E−6) | 3.25E−11 (±2.25E−12) |
| S764G-S766Y | 1.19E+07 (±9.1E5) | 2.63E−04 (±1.41E−5) | 2.29E−11 (±3.42E−12) |
| S766Y-P769R | 1.18E+07 (±4.1E5) | 2.75E−04 (±1.71E−5) | 2.32E−11 (±9.54E−13) |
| S766Y-P769K | 1.09E+07 (±1.37E6) | 2.85E−04 (±2.08E−5) | 2.68E−11 (±1.55E−12) |
| S766W-S806A | 8.88E+06 (±1.11E6) | 3.00E−04 (±1.9E−5) | 3.54E−11 (±4.37E−12) |
| S764Y-S766Y | 1.14E+07 (±1.71E6) | 3.34E−04 (±2.7E−5) | 3.07E−11 (±3.53E−12) |
| S766Y-S769N | 1.21E+07 (±1.11E6) | 3.48E−04 (±3.21E−5) | 2.89E−11 (±1.75E−12) |
| S764A | 1.26E+07 (±1.38E6) | 6.38E−04 (±3.24E−5) | 5.14E−11 (±2.81E−12) |
| WT | 1.89E+07 (±2.68E6) | 1.47E−03 (±8.92E−5) | 8.25E−11 (±7.94E−12) |

TABLE 21

Dimers Binding to FVIII (pH 5.5)

| Mutant | ka (1/Ms) | kd (1/s) | KD (M) |
|---|---|---|---|
| S764P-S766I | 3.10E+06 (±3.05E5) | 1.81E−03 (±6.34E−5) | 5.98E−10 (±4.93E−11) |
| S764P-S766W | 3.02E+06 (±2.39E5) | 1.88E−03 (±1.78E−5) | 6.37E−10 (±5.75E−11) |
| S764E-S766Y | 2.43E+06 (±1.6E5) | 2.71E−03 (±9.8E−5) | 1.12E−09 (±5.29E−11) |
| S764Y-S766Y | 3.22E+06 (±1.24E5) | 3.45E−03 (±9.01E−5) | 1.07E−09 (±4.67E−11) |
| S766Y-P769R | 4.66E+06 (±1.47E5) | 6.54E−03 (±2.02E−4) | 1.40E−09 (±2.29E−11) |
| S764I-S766W | 3.28E+06 (±1.22E5) | 7.24E−03 (±2.89E−4) | 2.21E−09 (±5.78E−11) |
| S766Y-P769K | 4.14E+06 (±2.95E5) | 7.40E−03 (±3.9E−4) | 1.79E−09 (±1.27E−10) |
| S766Y | 3.50E+06 (±2.5E5) | 7.40E−03 (±2.12E−3) | 2.92E−09 (±1.38E−10) |
| S766Y-S769N | 2.05E+06 (±2.02E5) | 1.02E−02 (±7.84E−4) | 5.01E−09 (±2.67E−10) |
| S766W-S806A | 8.13E+05 (±2.83E5) | 1.40E−02 (±6.74E−4) | 1.43E−08 (±2.38E−9) |
| S764G-S766Y | 2.66E+06 (±4.55E5) | 1.85E−02 (±1.12E−3) | 7.53E−09 (±1.15E−9) |
| S764A | 2.25E+06 (±1.42E6) | 4.01E−02 (±2.54E−3) | 5.26E−08 (±3.33E−9) |
| WT | 1.37E+06 (±2.44E5) | 4.26E−02 (±3.9E−3) | 3.54E−08 (±2.89E−9) |

The invention claimed is:

1. A modified polypeptide which binds Factor VIII, wherein the modified polypeptide comprises the amino acid sequence selected from the group consisting of SEQ ID NOs: 5-17.

2. The modified polypeptide of claim 1, wherein the modified polypeptide binds to Factor VIII with an off rate at least 5 fold lower than a reference polypeptide comprising the amino acid sequence of SEQ ID NO: 3.

3. The modified polypeptide of claim 1, further comprising a half-life enhancing protein (HLEP).

4. The modified polypeptide of claim 3, wherein the HLEP is an albumin.

5. The modified polypeptide of claim 4, wherein the N-terminus of the albumin is fused to the C-terminus of the modified polypeptide either directly or via a spacer.

6. A method of treating a bleeding disorder, comprising administering to a patient in need thereof a therapeutically effective amount of one or more modified polypeptides of claim 1.

7. The method of claim 6, wherein the bleeding disorder is von Willebrand's disease or hemophilia A.

8. A method of increasing the Factor VIII binding affinity of von Willebrand Factor (VWF), comprising modifying the D' domain of the VWF to comprise the amino acid sequence selected from any one of SEQ ID NOs: 5-17.

* * * * *

SEQUENCE LISTING

<160> NUMBER OF SEQ ID NOS: 20

<210> SEQ ID NO 1
<211> LENGTH: 8442

<212> TYPE: DNA
<213> ORGANISM: Homo sapiens

<400> SEQUENCE: 1

| | | | | | |
|---|---|---|---|---|---|
| atgattcctg | ccagatttgc | cggggtgctg | cttgctctgg | ccctcatttt | gccagggacc | 60 |
| ctttgtgcag | aaggaactcg | cggcaggtca | tccacggccc | gatgcagcct | tttcggaagt | 120 |
| gacttcgtca | acacctttga | tgggagcatg | tacagctttg | cgggatactg | cagttacctc | 180 |
| ctggcagggg | gctgccagaa | acgctccttc | tcgattattg | ggacttcca | gaatggcaag | 240 |
| agagtgagcc | tctccgtgta | tcttggggaa | ttttttgaca | tccatttgtt | tgtcaatggt | 300 |
| accgtgacac | aggggaccca | agagtctccc | atgccctatg | cctccaaagg | gctgtatcta | 360 |
| gaaactgagg | ctgggtacta | caagctgtcc | ggtgaggcct | atggctttgt | ggccaggatc | 420 |
| gatggcagcg | gcaactttca | agtcctgctg | tcagacagat | acttcaacaa | gacctgcggg | 480 |
| ctgtgtggca | actttaacat | ctttgctgaa | gatgacttta | tgacccaaga | agggaccttg | 540 |
| acctcggacc | cttatgactt | tgccaactca | tgggctctga | gcagtggaga | cagtggtgt | 600 |
| gaacgggcat | ctcctcccag | cagctcatgc | aacatctcct | ctggggaaat | gcagaagggc | 660 |
| ctgtgggagc | agtgccagct | tctgaagagc | acctcggtgt | ttgcccgctg | ccaccctctg | 720 |
| gtggaccccg | agccttttgt | ggccctgtgt | gagaagactt | tgtgtgagtg | tgctgggggg | 780 |
| ctggagtgcg | cctgccctgc | cctcctggag | tacgcccgga | cctgtgccca | ggagggaatg | 840 |
| gtgctgtacg | gctggaccga | ccacagcgcg | tgcagcccag | tgtgccctgc | tggtatggag | 900 |
| tataggcagt | gtgtgtcccc | ttgcgccagg | acctgccaga | gcctgcacat | caatgaaatg | 960 |
| tgtcaggagc | gatgcgtgga | tggctgcagc | tgccctgagg | acagctcct | ggatgaaggc | 1020 |
| ctctgcgtgg | agagcaccga | gtgtcctgc | gtgcattccg | gaaagcgcta | ccctcccggc | 1080 |
| acctccctct | ctcgagactg | caacctgc | atttgccgaa | acagccagtg | gatctgcagc | 1140 |
| aatgaagaat | gtccagggga | gtgccttgtc | acaggtcaat | cacacttcaa | gagctttgac | 1200 |
| aacagatact | tcaccttcag | tgggatctgc | cagtacctgc | tggcccggga | ttgccaggac | 1260 |
| cactccttct | ccattgtcat | tgagactgtc | cagtgtgctg | atgaccgcga | cgctgtgtgc | 1320 |
| acccgctccg | tcaccgtccg | gctgcctggc | ctgcacaaca | gccttgtgaa | actgaagcat | 1380 |
| ggggcaggag | ttgccatgga | tggccaggac | gtccagctcc | ccctcctgaa | aggtgacctc | 1440 |
| cgcatccagc | atacagtgac | ggcctccgtg | cgcctcagct | acggggagga | cctgcagatg | 1500 |
| gactgggatg | ccgcgggag | gctgctggtg | aagctgtccc | ccgtctatgc | cgggaagacc | 1560 |
| tgcggcctgt | gtgggaatta | caatggcaac | cagggcgacg | acttccttac | ccctctgggg | 1620 |
| ctggcggagc | cccgggtgga | ggacttcggg | aacgcctgga | agctgcacgg | ggactgccag | 1680 |
| gacctgcaga | agcagcacag | cgatccctgc | gccctcaacc | cgcgcatgac | caggttctcc | 1740 |
| gaggaggcgt | gcgcggtcct | gacgtcccc | acattcgagg | cctgccatcg | tgccgtcagc | 1800 |
| ccgctgccct | acctgcggaa | ctgccgctac | gacgtgtgct | cctgctcgga | cggccgcgag | 1860 |
| tgcctgtgcg | gcgccctggc | cagctatgcc | gcggcctgcg | cggggagagg | cgtgcgcgtc | 1920 |
| gcgtggcgcg | agccaggccg | ctgtgagctg | aactgcccga | aggccaggt | gtacctgcag | 1980 |
| tgcgggaccc | cctgcaacct | gacctgccgc | tctctctctt | acccggatga | ggaatgcaat | 2040 |
| gaggcctgcc | tggagggctg | cttctgcccc | ccagggctct | acatggatga | gaggggggac | 2100 |
| tgcgtgccca | aggcccagtg | ccctgttac | tatgacggtg | agatcttcca | gccagaagac | 2160 |
| atcttctcag | accatcacac | catgtgctac | tgtgaggatg | gcttcatgca | ctgtaccatg | 2220 |

```
agtggagtcc ccggaagctt gctgcctgac gctgtcctca gcagtcccct gtctcatcgc    2280
agcaaaagga gcctatcctg tcggcccccc atggtcaagc tggtgtgtcc cgctgacaac    2340
ctgcgggctg aagggctcga gtgtaccaaa acgtgccaga actatgacct ggagtgcatg    2400
agcatgggct gtgtctctgg ctgcctctgc cccccgggca tggtccggca tgagaacaga    2460
tgtgtggccc tggaaaggtg tccctgcttc catcagggca aggagtatgc ccctggagaa    2520
acagtgaaga ttggctgcaa cacttgtgtc tgtcgggacc ggaagtggaa ctgcacagac    2580
catgtgtgtg atgccacgtg ctccacgatc ggcatggccc actacctcac cttcgacggg    2640
ctcaaatacc tgttccccgg ggagtgccag tacgttctgg tgcaggatta ctgcggcagt    2700
aaccctggga cctttcggat cctagtgggg aataagggat gcagccaccc ctcagtgaaa    2760
tgcaagaaac gggtcaccat cctggtggag ggaggagaga ttgagctgtt tgacggggag    2820
gtgaatgtga agaggcccat gaaggatgag actcactttg aggtggtgga gtctggccgg    2880
tacatcattc tgctgctggg caaagccctc tccgtggtct gggaccgcca cctgagcatc    2940
tccgtggtcc tgaagcagac ataccaggag aaagtgtgtg cctgtgtgg gaattttgat    3000 ggcatccaga acaatgacct caccagcagc aacctccaag tggaggaaga ccctgtggac    3060
tttgggaact cctggaaagt gagctcgcag tgtgctgaca ccagaaaagt gcctctggac    3120
tcatcccctg ccacctgcca taacaacatc atgaagcaga cgatggtgga ttcctcctgt    3180
agaatcctta ccagtgacgt cttccaggac tgcaacaagc tggtggaccc cgagccatat    3240
ctggatgtct gcatttacga cacctgctcc tgtgagtcca ttggggactg cgcctgcttc    3300
tgcgacacca ttgctgccta tgcccacgtg tgtgcccagc atggcaaggt ggtgacctgg    3360
aggacggcca cattgtgccc ccagagctgc gaggagagga atctccggga aacgggtat    3420 gagtgtgagt ggcgctataa cagctgtgca cctgcctgtc aagtcacgtg tcagcaccct    3480
gagccactgg cctgccctgt gcagtgtgtg gagggctgcc atgcccactg ccctccaggg    3540
aaaatcctgg atgagctttt gcagacctgc gttgaccctg aagactgtcc agtgtgtgag    3600
gtggctggcc ggcgttttgc ctcaggaaag aaagtcacct tgaatcccag tgaccctgag    3660
cactgccaga tttgccactg tgatgttgtc aacctcacct gtgaagcctg ccaggagccg    3720
ggaggcctgg tggtgcctcc cacagatgcc ccggtgagcc ccaccactct gtatgtggag    3780
gacatctcgg aaccgccgtt gcacgatttc tactgcagca ggctactgga cctggtcttc    3840
ctgctggatg gctcctccag gctgtccgag gctgagtttg aagtgctgaa ggcctttgtg    3900
gtggacatga tggagcggct gcgcatctcc cagaagtggg tccgcgtggc cgtggtggag    3960
taccacgacg gctcccacgc ctacatcggg ctcaaggacc ggaagcgacc gtcagagctg    4020
cggcgcattg ccagccaggt gaagtatgcg ggcagccagg tggcctccac cagcgaggtc    4080
ttgaaataca cactgttcca aatcttcagc aagatcgacc gccctgaagc ctcccgcatc    4140
gccctgctcc tgatggccag ccaggagccc caacggatgt cccggaactt tgtccgctac    4200
gtccagggcc tgaagaagaa gaaggtcatt gtgatcccgg tgggcattgg ccccatgcc    4260 aacctcaagc agatccgcct catcgagaag caggcccctg agaacaaggc cttcgtgctg    4320
agcagtgtgg atgagctgga gcagcaaagg gacgagatcg ttagctacct ctgtgacctt    4380
gcccctgaag cccctcctcc tactctgccc ccccacatgg cacaagtcac tgtgggcccg    4440
gggctcttgg ggtttcgac cctggggccc aagaggaact ccatggttct ggatgtggcg    4500
ttcgtcctga aggatcgga caaaattggt gaagccgact tcaacaggag caaggagttc    4560
atggaggagg tgattcagcg gatggatgtg gccaggaaca gcatccacgt cacggtgctg    4620
```

```
cagtactcct acatggtgac cgtggagtac cccttcagcg aggcacagtc caaagggac    4680
atcctgcagc gggtgcgaga gatccgctac cagggcggca acaggaccaa cactgggctg   4740
gccctgcggt acctctctga ccacagcttc ttggtcagcc agggtgaccg ggagcaggcg   4800
cccaacctgg tctacatggt caccggaaat cctgcctctg atgagatcaa gaggctgcct   4860
ggagacatcc aggtggtgcc cattggagtg ggccctaatg ccaacgtgca ggagctggag   4920
aggattggct ggcccaatgc ccctatcctc atccaggact tgagacgct ccccgagag    4980
gctcctgacc tggtgctgca gaggtgctgc tccggagagg ggctgcagat ccccaccctc   5040
tcccctgcac ctgactgcag ccagcccctg gacgtgatcc ttctcctgga tggctcctcc   5100
agtttcccag cttcttattt tgatgaaatg aagagtttcg ccaaggcttt catttcaaaa   5160
gccaatatag ggcctcgtct cactcaggtg tcagtgctgc agtatggaag catcaccacc   5220
attgacgtgc catggaacgt ggtcccggag aaagcccatt tgctgagcct tgtggacgtc   5280
atgcagcggg agggaggccc cagccaaatc ggggatgcct tgggctttgc tgtgcgatac   5340
ttgacttcag aaatgcatgg ggcgcgcccg ggagcctcaa aggcggtggt catcctggtc   5400
acggacgtct ctgtggattc agtggatgca gcagctgatg ccgccaggtc caacagagtg   5460
acagtgttcc ctattggaat tggagatcgc tacgatgcag cccagctacg atcttggca   5520
ggcccagcag gcgactccaa cgtggtgaag ctccagcgaa tcgaagacct ccctaccatg   5580
gtcaccttgg gcaattcctt cctccacaaa ctgtgctctg gatttgttag gatttgcatg   5640
gatgaggatg ggaatgagaa gaggcccggg gacgtctgga ccttgccaga ccagtgccac   5700
accgtgactt gccagccaga tggccagacc ttgctgaaga gtcatcgggt caactgtgac   5760
cgggggctga ggccttcgtg ccctaacagc cagtcccctg ttaaagtgga agagacctgt   5820
ggctgccgct ggacctgccc ctgcgtgtgc acaggcagct ccactcggca tcgtgacc    5880
tttgatgggc agaatttcaa gctgactggc agctgttctt atgtcctatt tcaaaacaag   5940
gagcaggacc tggaggtgat tctccataat ggtgcctgca gccctggagc aaggcagggc   6000
tgcatgaaat ccatcgaggt gaagcacagt gccctctccg tcgagctgca cagtgacatg   6060
gaggtgacgg tgaatgggag actggtctct gttccttacg tgggtgggaa catggaagtc   6120
aacgtttatg gtgccatcat gcatgaggtc agattcaatc accttggtca catcttcaca   6180
ttcactccac aaaacaatga gttccaactg cagctcagcc caagacttt tgcttcaaag   6240
acgtatggtc tgtgtgggat ctgtgatgag aacggagcca atgacttcat gctgagggat   6300
ggcacagtca cccagactg gaaaacactt gttcaggaat ggactgtgca gcggccaggg   6360
cagacgtgcc agcccatcct ggaggagcag tgtcttgtcc ccgacagctc ccactgccag   6420
gtcctcctct taccactgtt tgctgaatgc acaaggtcc tggctccagc cacattctat   6480
gccatctgcc agcaggacag ttgccaccag gagcaagtgt gtgaggtgat cgcctcttat   6540
gcccacctct gtcggaccaa cggggtctgc gttgactgga ggacacctga tttctgtgct   6600
atgtcatgcc caccatctct ggtttataac cactgtgagc atggctgtcc ccggcactgt   6660
gatggcaacg tgagctcctg tgggaccat ccctccgaag ctgtttctg ccctccagat    6720
aaagtcatgt tggaaggcag ctgtgtccct gaagaggcct gcactcagtg cattggtgag   6780
gatggagtcc agcaccagtt cctggaagcc tgggtcccgg accaccagcc tgtcagatc   6840
tgcacatgcc tcagcgggcg gaaggtcaac tgcacaacgc agcccctgcc cacggccaaa   6900
gctcccacgt gtggcctgtg tgaagtagcc cgcctccgcc agaatgcaga ccagtgctgc   6960
```

```
cccgagtatg agtgtgtgtg tgacccagtg agctgtgacc tgcccccagt gcctcactgt    7020
gaacgtggcc tccagcccac actgaccaac cctggcgagt gcagacccaa cttcacctgc    7080
gcctgcagga aggaggagtg caaaagagtg tccccaccct cctgccccccc gcaccgtttg   7140
cccacccttc ggaagaccca gtgctgtgat gagtatgagt gtgcctgcaa ctgtgtcaac    7200
tccacagtga gctgtcccct tgggtacttg gcctcaaccg ccaccaatga ctgtggctgt    7260
accacaacca cctgccttcc cgacaaggtg tgtgtccacc gaagcaccat ctaccctgtg    7320
ggccagttct ggcgaggggg ctgcgatgtg tgcacctgca ccgacatgga ggatgccgtg    7380
atgggcctcc gcgtggccca gtgctcccag aagccctgtg aggacagctg tcggtcgggc    7440
ttcacttacg ttctgcatga aggcgagtgc tgtggaaggt gcctgccatc tgcctgtgag    7500
gtggtgactg gctcaccgcg gggggactcc cagtcttcct ggaagagtgt cggctcccag    7560
tgggcctccc cggagaaccc ctgcctcatc aatgagtgtg tccgagtgaa ggaggaggtc    7620
tttatacaac aaaggaacgt ctcctgcccc cagctggagg tccctgtctg cccctcgggc    7680
tttcagctga gctgtaagac ctcagcgtgc tgcccaagct gtcgctgtga gcgcatggag    7740
gcctgcatgc tcaatggcac tgtcattggg cccgggaaga ctgtgatgat cgatgtgtgc    7800
acgacctgcc gctgcatggt gcaggtgggg gtcatctctg gattcaagct ggagtgcagg    7860
aagaccacct gcaaccctg cccctgggt tacaaggaag aaaataacac aggtgaatgt     7920
tgtgggagat gtttgcctac ggcttgcacc attcagctaa gaggaggaca gatcatgaca    7980
ctgaagcgtg atgagacgct ccaggatggc tgtgatactc acttctgcaa ggtcaatgag    8040
agaggagagt acttctggga gaagagggtc acaggctgcc cacccttga tgaacacaag     8100
tgtctggctg agggaggtaa aattatgaaa attccaggca cctgctgtga cacatgtgag    8160
gagcctgagt gcaacgacat cactgccagg ctgcagtatg tcaaggtggg aagctgtaag    8220
tctgaagtag aggtggatat ccactactgc cagggcaaat gtgccagcaa agccatgtac    8280
tccattgaca tcaacgatgt gcaggaccag tgctcctgct gctctccgac acggacggaa    8340
cccatgcagg tggccctgca ctgcaccaat ggctctgttg tgtaccatga ggttctcaat    8400
gccatggagt gcaaatgctc ccccaggaag tgcagcaagt ga                       8442
```

<210> SEQ ID NO 2
<211> LENGTH: 2813
<212> TYPE: PRT
<213> ORGANISM: Homo sapiens

<400> SEQUENCE: 2

```
Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110
```

```
Tyr Ala Ser Lys Gly Leu Tyr Leu Glu Thr Glu Ala Gly Tyr Tyr Lys
            115                 120                 125
Leu Ser Gly Glu Ala Tyr Gly Phe Val Ala Arg Ile Asp Gly Ser Gly
    130                 135                 140
Asn Phe Gln Val Leu Leu Ser Asp Arg Tyr Phe Asn Lys Thr Cys Gly
145                 150                 155                 160
Leu Cys Gly Asn Phe Asn Ile Phe Ala Glu Asp Asp Phe Met Thr Gln
                165                 170                 175
Glu Gly Thr Leu Thr Ser Asp Pro Tyr Asp Phe Ala Asn Ser Trp Ala
            180                 185                 190
Leu Ser Ser Gly Glu Gln Trp Cys Glu Arg Ala Ser Pro Pro Ser Ser
    195                 200                 205
Ser Cys Asn Ile Ser Ser Gly Glu Met Gln Lys Gly Leu Trp Glu Gln
210                 215                 220
Cys Gln Leu Leu Lys Ser Thr Ser Val Phe Ala Arg Cys His Pro Leu
225                 230                 235                 240
Val Asp Pro Glu Pro Phe Val Ala Leu Cys Glu Lys Thr Leu Cys Glu
                245                 250                 255
Cys Ala Gly Gly Leu Glu Cys Ala Cys Pro Ala Leu Leu Glu Tyr Ala
            260                 265                 270
Arg Thr Cys Ala Gln Glu Gly Met Val Leu Tyr Gly Trp Thr Asp His
    275                 280                 285
Ser Ala Cys Ser Pro Val Cys Pro Ala Gly Met Glu Tyr Arg Gln Cys
290                 295                 300
Val Ser Pro Cys Ala Arg Thr Cys Gln Ser Leu His Ile Asn Glu Met
305                 310                 315                 320
Cys Gln Glu Arg Cys Val Asp Gly Cys Ser Cys Pro Glu Gly Gln Leu
                325                 330                 335
Leu Asp Glu Gly Leu Cys Val Glu Ser Thr Glu Cys Pro Cys Val His
            340                 345                 350
Ser Gly Lys Arg Tyr Pro Pro Gly Thr Ser Leu Ser Arg Asp Cys Asn
    355                 360                 365
Thr Cys Ile Cys Arg Asn Ser Gln Trp Ile Cys Ser Asn Glu Glu Cys
370                 375                 380
Pro Gly Glu Cys Leu Val Thr Gly Gln Ser His Phe Lys Ser Phe Asp
385                 390                 395                 400
Asn Arg Tyr Phe Thr Phe Ser Gly Ile Cys Gln Tyr Leu Leu Ala Arg
                405                 410                 415
Asp Cys Gln Asp His Ser Phe Ser Ile Val Ile Glu Thr Val Gln Cys
            420                 425                 430
Ala Asp Asp Arg Asp Ala Val Cys Thr Arg Ser Val Thr Val Arg Leu
    435                 440                 445
Pro Gly Leu His Asn Ser Leu Val Lys Leu Lys His Gly Ala Gly Val
450                 455                 460
Ala Met Asp Gly Gln Asp Val Gln Leu Pro Leu Leu Lys Gly Asp Leu
465                 470                 475                 480
Arg Ile Gln His Thr Val Thr Ala Ser Val Arg Leu Ser Tyr Gly Glu
                485                 490                 495
Asp Leu Gln Met Asp Trp Asp Gly Arg Gly Arg Leu Leu Val Lys Leu
            500                 505                 510
Ser Pro Val Tyr Ala Gly Lys Thr Cys Gly Leu Cys Gly Asn Tyr Asn
    515                 520                 525
Gly Asn Gln Gly Asp Asp Phe Leu Thr Pro Ser Gly Leu Ala Glu Pro
```

```
                530               535               540
Arg Val Glu Asp Phe Gly Asn Ala Trp Lys Leu His Gly Asp Cys Gln
545                 550               555               560

Asp Leu Gln Lys Gln His Ser Asp Pro Cys Ala Leu Asn Pro Arg Met
                565               570               575

Thr Arg Phe Ser Glu Glu Ala Cys Ala Val Leu Thr Ser Pro Thr Phe
                580               585               590

Glu Ala Cys His Arg Ala Val Ser Pro Leu Pro Tyr Leu Arg Asn Cys
                595               600               605

Arg Tyr Asp Val Cys Ser Cys Ser Asp Gly Arg Glu Cys Leu Cys Gly
                610               615               620

Ala Leu Ala Ser Tyr Ala Ala Ala Cys Ala Gly Arg Gly Val Arg Val
625               630               635               640

Ala Trp Arg Glu Pro Gly Arg Cys Glu Leu Asn Cys Pro Lys Gly Gln
                645               650               655

Val Tyr Leu Gln Cys Gly Thr Pro Cys Asn Leu Thr Cys Arg Ser Leu
                660               665               670

Ser Tyr Pro Asp Glu Glu Cys Asn Glu Ala Cys Leu Glu Gly Cys Phe
                675               680               685

Cys Pro Pro Gly Leu Tyr Met Asp Glu Arg Gly Asp Cys Val Pro Lys
                690               695               700

Ala Gln Cys Pro Cys Tyr Tyr Asp Gly Glu Ile Phe Gln Pro Glu Asp
705               710               715               720

Ile Phe Ser Asp His His Thr Met Cys Tyr Cys Glu Asp Gly Phe Met
                725               730               735

His Cys Thr Met Ser Gly Val Pro Gly Ser Leu Leu Pro Asp Ala Val
                740               745               750

Leu Ser Ser Pro Leu Ser His Arg Ser Lys Arg Ser Leu Ser Cys Arg
                755               760               765

Pro Pro Met Val Lys Leu Val Cys Pro Ala Asp Asn Leu Arg Ala Glu
                770               775               780

Gly Leu Glu Cys Thr Lys Thr Cys Gln Asn Tyr Asp Leu Glu Cys Met
785               790               795               800

Ser Met Gly Cys Val Ser Gly Cys Leu Cys Pro Pro Gly Met Val Arg
                805               810               815

His Glu Asn Arg Cys Val Ala Leu Glu Arg Cys Pro Cys Phe His Gln
                820               825               830

Gly Lys Glu Tyr Ala Pro Gly Glu Thr Val Lys Ile Gly Cys Asn Thr
                835               840               845

Cys Val Cys Arg Asp Arg Lys Trp Asn Cys Thr Asp His Val Cys Asp
850               855               860

Ala Thr Cys Ser Thr Ile Gly Met Ala His Tyr Leu Thr Phe Asp Gly
865               870               875               880

Leu Lys Tyr Leu Phe Pro Gly Glu Cys Gln Tyr Val Leu Val Gln Asp
                885               890               895

Tyr Cys Gly Ser Asn Pro Gly Thr Phe Arg Ile Leu Val Gly Asn Lys
                900               905               910

Gly Cys Ser His Pro Ser Val Lys Cys Lys Lys Arg Val Thr Ile Leu
                915               920               925

Val Glu Gly Gly Glu Ile Glu Leu Phe Asp Gly Glu Val Asn Val Lys
                930               935               940

Arg Pro Met Lys Asp Glu Thr His Phe Glu Val Val Glu Ser Gly Arg
945               950               955               960
```

```
Tyr Ile Ile Leu Leu Leu Gly Lys Ala Leu Ser Val Val Trp Asp Arg
                965                 970                 975
His Leu Ser Ile Ser Val Val Leu Lys Gln Thr Tyr Gln Glu Lys Val
                980                 985                 990
Cys Gly Leu Cys Gly Asn Phe Asp Gly Ile Gln Asn Asn Asp Leu Thr
                995                1000                1005
Ser Ser Asn Leu Gln Val Glu Glu Asp Pro Val Asp Phe Gly Asn
            1010                1015                1020
Ser Trp Lys Val Ser Ser Gln Cys Ala Asp Thr Arg Lys Val Pro
            1025                1030                1035
Leu Asp Ser Ser Pro Ala Thr Cys His Asn Asn Ile Met Lys Gln
            1040                1045                1050
Thr Met Val Asp Ser Ser Cys Arg Ile Leu Thr Ser Asp Val Phe
            1055                1060                1065
Gln Asp Cys Asn Lys Leu Val Asp Pro Glu Pro Tyr Leu Asp Val
            1070                1075                1080
Cys Ile Tyr Asp Thr Cys Ser Cys Glu Ser Ile Gly Asp Cys Ala
            1085                1090                1095
Cys Phe Cys Asp Thr Ile Ala Ala Tyr Ala His Val Cys Ala Gln
            1100                1105                1110
His Gly Lys Val Val Thr Trp Arg Thr Ala Thr Leu Cys Pro Gln
            1115                1120                1125
Ser Cys Glu Glu Arg Asn Leu Arg Glu Asn Gly Tyr Glu Cys Glu
            1130                1135                1140
Trp Arg Tyr Asn Ser Cys Ala Pro Ala Cys Gln Val Thr Cys Gln
            1145                1150                1155
His Pro Glu Pro Leu Ala Cys Pro Val Gln Cys Val Glu Gly Cys
            1160                1165                1170
His Ala His Cys Pro Pro Gly Lys Ile Leu Asp Glu Leu Leu Gln
            1175                1180                1185
Thr Cys Val Asp Pro Glu Asp Cys Pro Val Cys Glu Val Ala Gly
            1190                1195                1200
Arg Arg Phe Ala Ser Gly Lys Lys Val Thr Leu Asn Pro Ser Asp
            1205                1210                1215
Pro Glu His Cys Gln Ile Cys His Cys Asp Val Val Asn Leu Thr
            1220                1225                1230
Cys Glu Ala Cys Gln Glu Pro Gly Gly Leu Val Val Pro Pro Thr
            1235                1240                1245
Asp Ala Pro Val Ser Pro Thr Thr Leu Tyr Val Glu Asp Ile Ser
            1250                1255                1260
Glu Pro Pro Leu His Asp Phe Tyr Cys Ser Arg Leu Leu Asp Leu
            1265                1270                1275
Val Phe Leu Leu Asp Gly Ser Ser Arg Leu Ser Glu Ala Glu Phe
            1280                1285                1290
Glu Val Leu Lys Ala Phe Val Val Asp Met Met Glu Arg Leu Arg
            1295                1300                1305
Ile Ser Gln Lys Trp Val Arg Val Ala Val Val Glu Tyr His Asp
            1310                1315                1320
Gly Ser His Ala Tyr Ile Gly Leu Lys Asp Arg Lys Arg Pro Ser
            1325                1330                1335
Glu Leu Arg Arg Ile Ala Ser Gln Val Lys Tyr Ala Gly Ser Gln
            1340                1345                1350
```

```
Val Ala Ser Thr Ser Glu Val Leu Lys Tyr Thr Leu Phe Gln Ile
    1355                1360                1365

Phe Ser Lys Ile Asp Arg Pro Glu Ala Ser Arg Ile Thr Leu Leu
    1370                1375                1380

Leu Met Ala Ser Gln Glu Pro Gln Arg Met Ser Arg Asn Phe Val
    1385                1390                1395

Arg Tyr Val Gln Gly Leu Lys Lys Lys Val Ile Val Ile Pro
    1400                1405                1410

Val Gly Ile Gly Pro His Ala Asn Leu Lys Gln Ile Arg Leu Ile
    1415                1420                1425

Glu Lys Gln Ala Pro Glu Asn Lys Ala Phe Val Leu Ser Ser Val
    1430                1435                1440

Asp Glu Leu Glu Gln Gln Arg Asp Glu Ile Val Ser Tyr Leu Cys
    1445                1450                1455

Asp Leu Ala Pro Glu Ala Pro Pro Pro Thr Leu Pro Pro Asp Met
    1460                1465                1470

Ala Gln Val Thr Val Gly Pro Gly Leu Leu Gly Val Ser Thr Leu
    1475                1480                1485

Gly Pro Lys Arg Asn Ser Met Val Leu Asp Val Ala Phe Val Leu
    1490                1495                1500

Glu Gly Ser Asp Lys Ile Gly Glu Ala Asp Phe Asn Arg Ser Lys
    1505                1510                1515

Glu Phe Met Glu Glu Val Ile Gln Arg Met Asp Val Gly Gln Asp
    1520                1525                1530

Ser Ile His Val Thr Val Leu Gln Tyr Ser Tyr Met Val Thr Val
    1535                1540                1545

Glu Tyr Pro Phe Ser Glu Ala Gln Ser Lys Gly Asp Ile Leu Gln
    1550                1555                1560

Arg Val Arg Glu Ile Arg Tyr Gln Gly Gly Asn Arg Thr Asn Thr
    1565                1570                1575

Gly Leu Ala Leu Arg Tyr Leu Ser Asp His Ser Phe Leu Val Ser
    1580                1585                1590

Gln Gly Asp Arg Glu Gln Ala Pro Asn Leu Val Tyr Met Val Thr
    1595                1600                1605

Gly Asn Pro Ala Ser Asp Glu Ile Lys Arg Leu Pro Gly Asp Ile
    1610                1615                1620

Gln Val Val Pro Ile Gly Val Gly Pro Asn Ala Asn Val Gln Glu
    1625                1630                1635

Leu Glu Arg Ile Gly Trp Pro Asn Ala Pro Ile Leu Ile Gln Asp
    1640                1645                1650

Phe Glu Thr Leu Pro Arg Glu Ala Pro Asp Leu Val Leu Gln Arg
    1655                1660                1665

Cys Cys Ser Gly Glu Gly Leu Gln Ile Pro Thr Leu Ser Pro Ala
    1670                1675                1680

Pro Asp Cys Ser Gln Pro Leu Asp Val Ile Leu Leu Leu Asp Gly
    1685                1690                1695

Ser Ser Ser Phe Pro Ala Ser Tyr Phe Asp Glu Met Lys Ser Phe
    1700                1705                1710

Ala Lys Ala Phe Ile Ser Lys Ala Asn Ile Gly Pro Arg Leu Thr
    1715                1720                1725

Gln Val Ser Val Leu Gln Tyr Gly Ser Ile Thr Thr Ile Asp Val
    1730                1735                1740

Pro Trp Asn Val Val Pro Glu Lys Ala His Leu Leu Ser Leu Val
```

-continued

```
            1745                1750                1755

Asp Val Met Gln Arg Glu Gly Pro Ser Gln Ile Gly Asp Ala
            1760                1765                1770

Leu Gly Phe Ala Val Arg Tyr Leu Thr Ser Glu Met His Gly Ala
            1775                1780                1785

Arg Pro Gly Ala Ser Lys Ala Val Val Ile Leu Val Thr Asp Val
            1790                1795                1800

Ser Val Asp Ser Val Asp Ala Ala Ala Asp Ala Ala Arg Ser Asn
            1805                1810                1815

Arg Val Thr Val Phe Pro Ile Gly Ile Gly Asp Arg Tyr Asp Ala
            1820                1825                1830

Ala Gln Leu Arg Ile Leu Ala Gly Pro Ala Gly Asp Ser Asn Val
            1835                1840                1845

Val Lys Leu Gln Arg Ile Glu Asp Leu Pro Thr Met Val Thr Leu
            1850                1855                1860

Gly Asn Ser Phe Leu His Lys Leu Cys Ser Gly Phe Val Arg Ile
            1865                1870                1875

Cys Met Asp Glu Asp Gly Asn Glu Lys Arg Pro Gly Asp Val Trp
            1880                1885                1890

Thr Leu Pro Asp Gln Cys His Thr Val Thr Cys Gln Pro Asp Gly
            1895                1900                1905

Gln Thr Leu Leu Lys Ser His Arg Val Asn Cys Asp Arg Gly Leu
            1910                1915                1920

Arg Pro Ser Cys Pro Asn Ser Gln Ser Pro Val Lys Val Glu Glu
            1925                1930                1935

Thr Cys Gly Cys Arg Trp Thr Cys Pro Cys Val Cys Thr Gly Ser
            1940                1945                1950

Ser Thr Arg His Ile Val Thr Phe Asp Gly Gln Asn Phe Lys Leu
            1955                1960                1965

Thr Gly Ser Cys Ser Tyr Val Leu Phe Gln Asn Lys Glu Gln Asp
            1970                1975                1980

Leu Glu Val Ile Leu His Asn Gly Ala Cys Ser Pro Gly Ala Arg
            1985                1990                1995

Gln Gly Cys Met Lys Ser Ile Glu Val Lys His Ser Ala Leu Ser
            2000                2005                2010

Val Glu Leu His Ser Asp Met Glu Val Thr Val Asn Gly Arg Leu
            2015                2020                2025

Val Ser Val Pro Tyr Val Gly Gly Asn Met Glu Val Asn Val Tyr
            2030                2035                2040

Gly Ala Ile Met His Glu Val Arg Phe Asn His Leu Gly His Ile
            2045                2050                2055

Phe Thr Phe Thr Pro Gln Asn Asn Glu Phe Gln Leu Gln Leu Ser
            2060                2065                2070

Pro Lys Thr Phe Ala Ser Lys Thr Tyr Gly Leu Cys Gly Ile Cys
            2075                2080                2085

Asp Glu Asn Gly Ala Asn Asp Phe Met Leu Arg Asp Gly Thr Val
            2090                2095                2100

Thr Thr Asp Trp Lys Thr Leu Val Gln Glu Trp Thr Val Gln Arg
            2105                2110                2115

Pro Gly Gln Thr Cys Gln Pro Ile Leu Glu Glu Gln Cys Leu Val
            2120                2125                2130

Pro Asp Ser Ser His Cys Gln Val Leu Leu Leu Pro Leu Phe Ala
            2135                2140                2145
```

-continued

Glu Cys His Lys Val Leu Ala Pro Ala Thr Phe Tyr Ala Ile Cys
2150                2155                2160

Gln Gln Asp Ser Cys His Gln Glu Gln Val Cys Glu Val Ile Ala
2165                2170                2175

Ser Tyr Ala His Leu Cys Arg Thr Asn Gly Val Cys Val Asp Trp
2180                2185                2190

Arg Thr Pro Asp Phe Cys Ala Met Ser Cys Pro Pro Ser Leu Val
2195                2200                2205

Tyr Asn His Cys Glu His Gly Cys Pro Arg His Cys Asp Gly Asn
2210                2215                2220

Val Ser Ser Cys Gly Asp His Pro Ser Glu Gly Cys Phe Cys Pro
2225                2230                2235

Pro Asp Lys Val Met Leu Glu Gly Ser Cys Val Pro Glu Glu Ala
2240                2245                2250

Cys Thr Gln Cys Ile Gly Glu Asp Gly Val Gln His Gln Phe Leu
2255                2260                2265

Glu Ala Trp Val Pro Asp His Gln Pro Cys Gln Ile Cys Thr Cys
2270                2275                2280

Leu Ser Gly Arg Lys Val Asn Cys Thr Thr Gln Pro Cys Pro Thr
2285                2290                2295

Ala Lys Ala Pro Thr Cys Gly Leu Cys Glu Val Ala Arg Leu Arg
2300                2305                2310

Gln Asn Ala Asp Gln Cys Cys Pro Glu Tyr Glu Cys Val Cys Asp
2315                2320                2325

Pro Val Ser Cys Asp Leu Pro Pro Val Pro His Cys Glu Arg Gly
2330                2335                2340

Leu Gln Pro Thr Leu Thr Asn Pro Gly Glu Cys Arg Pro Asn Phe
2345                2350                2355

Thr Cys Ala Cys Arg Lys Glu Glu Cys Lys Arg Val Ser Pro Pro
2360                2365                2370

Ser Cys Pro Pro His Arg Leu Pro Thr Leu Arg Lys Thr Gln Cys
2375                2380                2385

Cys Asp Glu Tyr Glu Cys Ala Cys Asn Cys Val Asn Ser Thr Val
2390                2395                2400

Ser Cys Pro Leu Gly Tyr Leu Ala Ser Thr Ala Thr Asn Asp Cys
2405                2410                2415

Gly Cys Thr Thr Thr Thr Cys Leu Pro Asp Lys Val Cys Val His
2420                2425                2430

Arg Ser Thr Ile Tyr Pro Val Gly Gln Phe Trp Glu Glu Gly Cys
2435                2440                2445

Asp Val Cys Thr Cys Thr Asp Met Glu Asp Ala Val Met Gly Leu
2450                2455                2460

Arg Val Ala Gln Cys Ser Gln Lys Pro Cys Glu Asp Ser Cys Arg
2465                2470                2475

Ser Gly Phe Thr Tyr Val Leu His Glu Gly Glu Cys Cys Gly Arg
2480                2485                2490

Cys Leu Pro Ser Ala Cys Glu Val Val Thr Gly Ser Pro Arg Gly
2495                2500                2505

Asp Ser Gln Ser Ser Trp Lys Ser Val Gly Ser Gln Trp Ala Ser
2510                2515                2520

Pro Glu Asn Pro Cys Leu Ile Asn Glu Cys Val Arg Val Lys Glu
2525                2530                2535

```
Glu Val Phe Ile Gln Gln Arg Asn Val Ser Cys Pro Gln Leu Glu
    2540                2545                2550

Val Pro Val Cys Pro Ser Gly Phe Gln Leu Ser Cys Lys Thr Ser
    2555                2560                2565

Ala Cys Cys Pro Ser Cys Arg Cys Glu Arg Met Glu Ala Cys Met
    2570                2575                2580

Leu Asn Gly Thr Val Ile Gly Pro Gly Lys Thr Val Met Ile Asp
    2585                2590                2595

Val Cys Thr Thr Cys Arg Cys Met Val Gln Val Gly Val Ile Ser
    2600                2605                2610

Gly Phe Lys Leu Glu Cys Arg Lys Thr Thr Cys Asn Pro Cys Pro
    2615                2620                2625

Leu Gly Tyr Lys Glu Glu Asn Asn Thr Gly Glu Cys Cys Gly Arg
    2630                2635                2640

Cys Leu Pro Thr Ala Cys Thr Ile Gln Leu Arg Gly Gly Gln Ile
    2645                2650                2655

Met Thr Leu Lys Arg Asp Glu Thr Leu Gln Asp Gly Cys Asp Thr
    2660                2665                2670

His Phe Cys Lys Val Asn Glu Arg Gly Glu Tyr Phe Trp Glu Lys
    2675                2680                2685

Arg Val Thr Gly Cys Pro Pro Phe Asp Glu His Lys Cys Leu Ala
    2690                2695                2700

Glu Gly Gly Lys Ile Met Lys Ile Pro Gly Thr Cys Cys Asp Thr
    2705                2710                2715

Cys Glu Glu Pro Glu Cys Asn Asp Ile Thr Ala Arg Leu Gln Tyr
    2720                2725                2730

Val Lys Val Gly Ser Cys Lys Ser Glu Val Glu Val Asp Ile His
    2735                2740                2745

Tyr Cys Gln Gly Lys Cys Ala Ser Lys Ala Met Tyr Ser Ile Asp
    2750                2755                2760

Ile Asn Asp Val Gln Asp Gln Cys Ser Cys Cys Ser Pro Thr Arg
    2765                2770                2775

Thr Glu Pro Met Gln Val Ala Leu His Cys Thr Asn Gly Ser Val
    2780                2785                2790

Val Tyr His Glu Val Leu Asn Ala Met Glu Cys Lys Cys Ser Pro
    2795                2800                2805

Arg Lys Cys Ser Lys
    2810

<210> SEQ ID NO 3
<211> LENGTH: 102
<212> TYPE: PRT
<213> ORGANISM: Homo sapiens

<400> SEQUENCE: 3

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
                20                  25                  30

Asp Leu Glu Cys Met Ser Met Gly Cys Val Ser Gly Cys Leu Cys Pro
            35                  40                  45

Pro Gly Met Val Arg His Glu Asn Arg Cys Val Ala Leu Glu Arg Cys
        50                  55                  60

Pro Cys Phe His Gln Gly Lys Glu Tyr Ala Pro Gly Glu Thr Val Lys
65                  70                  75                  80
```

-continued

Ile Gly Cys Asn Thr Cys Val Cys Arg Asp Arg Lys Trp Asn Cys Thr
            85                  90                  95

Asp His Val Cys Asp Ala
            100

<210> SEQ ID NO 4
<211> LENGTH: 2050
<212> TYPE: PRT
<213> ORGANISM: Homo sapiens

<400> SEQUENCE: 4

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly

```
                340                 345                 350
Lys Val Val Thr Trp Arg Thr Ala Thr Leu Cys Pro Gln Ser Cys Glu
        355                 360                 365
Glu Arg Asn Leu Arg Glu Asn Gly Tyr Glu Cys Glu Trp Arg Tyr Asn
        370                 375                 380
Ser Cys Ala Pro Ala Cys Gln Val Thr Cys Gln His Pro Glu Pro Leu
385                 390                 395                 400
Ala Cys Pro Val Gln Cys Val Glu Gly Cys His Ala His Cys Pro Pro
                405                 410                 415
Gly Lys Ile Leu Asp Glu Leu Leu Gln Thr Cys Val Asp Pro Glu Asp
            420                 425                 430
Cys Pro Val Cys Glu Val Ala Gly Arg Arg Phe Ala Ser Gly Lys Lys
                435                 440                 445
Val Thr Leu Asn Pro Ser Asp Pro Glu His Cys Gln Ile Cys His Cys
        450                 455                 460
Asp Val Val Asn Leu Thr Cys Glu Ala Cys Gln Glu Pro Gly Gly Leu
465                 470                 475                 480
Val Val Pro Pro Thr Asp Ala Pro Val Ser Pro Thr Thr Leu Tyr Val
                485                 490                 495
Glu Asp Ile Ser Glu Pro Pro Leu His Asp Phe Tyr Cys Ser Arg Leu
                500                 505                 510
Leu Asp Leu Val Phe Leu Leu Asp Gly Ser Ser Arg Leu Ser Glu Ala
            515                 520                 525
Glu Phe Glu Val Leu Lys Ala Phe Val Val Asp Met Met Glu Arg Leu
        530                 535                 540
Arg Ile Ser Gln Lys Trp Val Arg Val Ala Val Val Glu Tyr His Asp
545                 550                 555                 560
Gly Ser His Ala Tyr Ile Gly Leu Lys Asp Arg Lys Arg Pro Ser Glu
                565                 570                 575
Leu Arg Arg Ile Ala Ser Gln Val Lys Tyr Ala Gly Ser Gln Val Ala
            580                 585                 590
Ser Thr Ser Glu Val Leu Lys Tyr Thr Leu Phe Gln Ile Phe Ser Lys
        595                 600                 605
Ile Asp Arg Pro Glu Ala Ser Arg Ile Thr Leu Leu Leu Met Ala Ser
    610                 615                 620
Gln Glu Pro Gln Arg Met Ser Arg Asn Phe Val Arg Tyr Val Gln Gly
625                 630                 635                 640
Leu Lys Lys Lys Lys Val Ile Val Ile Pro Val Gly Ile Gly Pro His
                645                 650                 655
Ala Asn Leu Lys Gln Ile Arg Leu Ile Glu Lys Gln Ala Pro Glu Asn
            660                 665                 670
Lys Ala Phe Val Leu Ser Ser Val Asp Glu Leu Glu Gln Gln Arg Asp
        675                 680                 685
Glu Ile Val Ser Tyr Leu Cys Asp Leu Ala Pro Glu Ala Pro Pro Pro
        690                 695                 700
Thr Leu Pro Pro Asp Met Ala Gln Val Thr Val Gly Pro Gly Leu Leu
705                 710                 715                 720
Gly Val Ser Thr Leu Gly Pro Lys Arg Asn Ser Met Val Leu Asp Val
                725                 730                 735
Ala Phe Val Leu Glu Gly Ser Asp Lys Ile Gly Glu Ala Asp Phe Asn
            740                 745                 750
Arg Ser Lys Glu Phe Met Glu Glu Val Ile Gln Arg Met Asp Val Gly
        755                 760                 765
```

```
Gln Asp Ser Ile His Val Thr Val Leu Gln Tyr Ser Tyr Met Val Thr
    770             775                 780

Val Glu Tyr Pro Phe Ser Glu Ala Gln Ser Lys Gly Asp Ile Leu Gln
785             790                 795                 800

Arg Val Arg Glu Ile Arg Tyr Gln Gly Gly Asn Arg Thr Asn Thr Gly
                805                 810                 815

Leu Ala Leu Arg Tyr Leu Ser Asp His Ser Phe Leu Val Ser Gln Gly
            820                 825                 830

Asp Arg Glu Gln Ala Pro Asn Leu Val Tyr Met Val Thr Gly Asn Pro
        835                 840                 845

Ala Ser Asp Glu Ile Lys Arg Leu Pro Gly Asp Ile Gln Val Val Pro
    850                 855                 860

Ile Gly Val Gly Pro Asn Ala Asn Val Gln Glu Leu Glu Arg Ile Gly
865                 870                 875                 880

Trp Pro Asn Ala Pro Ile Leu Ile Gln Asp Phe Glu Thr Leu Pro Arg
                885                 890                 895

Glu Ala Pro Asp Leu Val Leu Gln Arg Cys Cys Ser Gly Glu Gly Leu
            900                 905                 910

Gln Ile Pro Thr Leu Ser Pro Ala Pro Asp Cys Ser Gln Pro Leu Asp
        915                 920                 925

Val Ile Leu Leu Leu Asp Gly Ser Ser Ser Phe Pro Ala Ser Tyr Phe
    930                 935                 940

Asp Glu Met Lys Ser Phe Ala Lys Ala Phe Ile Ser Lys Ala Asn Ile
945                 950                 955                 960

Gly Pro Arg Leu Thr Gln Val Ser Val Leu Gln Tyr Gly Ser Ile Thr
                965                 970                 975

Thr Ile Asp Val Pro Trp Asn Val Val Pro Glu Lys Ala His Leu Leu
            980                 985                 990

Ser Leu Val Asp Val Met Gln Arg Glu Gly Gly Pro Ser Gln Ile Gly
        995                 1000                1005

Asp Ala Leu Gly Phe Ala Val Arg Tyr Leu Thr Ser Glu Met His
    1010                1015                1020

Gly Ala Arg Pro Gly Ala Ser Lys Ala Val Val Ile Leu Val Thr
    1025                1030                1035

Asp Val Ser Val Asp Ser Val Asp Ala Ala Ala Asp Ala Ala Arg
    1040                1045                1050

Ser Asn Arg Val Thr Val Phe Pro Ile Gly Ile Gly Asp Arg Tyr
    1055                1060                1065

Asp Ala Ala Gln Leu Arg Ile Leu Ala Gly Pro Ala Gly Asp Ser
    1070                1075                1080

Asn Val Val Lys Leu Gln Arg Ile Glu Asp Leu Pro Thr Met Val
    1085                1090                1095

Thr Leu Gly Asn Ser Phe Leu His Lys Leu Cys Ser Gly Phe Val
    1100                1105                1110

Arg Ile Cys Met Asp Glu Asp Gly Asn Glu Lys Arg Pro Gly Asp
    1115                1120                1125

Val Trp Thr Leu Pro Asp Gln Cys His Thr Val Thr Cys Gln Pro
    1130                1135                1140

Asp Gly Gln Thr Leu Leu Lys Ser His Arg Val Asn Cys Asp Arg
    1145                1150                1155

Gly Leu Arg Pro Ser Cys Pro Asn Ser Gln Ser Pro Val Lys Val
    1160                1165                1170
```

```
Glu Glu Thr Cys Gly Cys Arg Trp Thr Cys Pro Cys Val Cys Thr
1175                1180                1185

Gly Ser Ser Thr Arg His Ile Val Thr Phe Asp Gly Gln Asn Phe
1190                1195                1200

Lys Leu Thr Gly Ser Cys Ser Tyr Val Leu Phe Gln Asn Lys Glu
1205                1210                1215

Gln Asp Leu Glu Val Ile Leu His Asn Gly Ala Cys Ser Pro Gly
1220                1225                1230

Ala Arg Gln Gly Cys Met Lys Ser Ile Glu Val Lys His Ser Ala
1235                1240                1245

Leu Ser Val Glu Leu His Ser Asp Met Glu Val Thr Val Asn Gly
1250                1255                1260

Arg Leu Val Ser Val Pro Tyr Val Gly Gly Asn Met Glu Val Asn
1265                1270                1275

Val Tyr Gly Ala Ile Met His Glu Val Arg Phe Asn His Leu Gly
1280                1285                1290

His Ile Phe Thr Phe Thr Pro Gln Asn Asn Glu Phe Gln Leu Gln
1295                1300                1305

Leu Ser Pro Lys Thr Phe Ala Ser Lys Thr Tyr Gly Leu Cys Gly
1310                1315                1320

Ile Cys Asp Glu Asn Gly Ala Asn Asp Phe Met Leu Arg Asp Gly
1325                1330                1335

Thr Val Thr Thr Asp Trp Lys Thr Leu Val Gln Glu Trp Thr Val
1340                1345                1350

Gln Arg Pro Gly Gln Thr Cys Gln Pro Ile Leu Glu Glu Gln Cys
1355                1360                1365

Leu Val Pro Asp Ser Ser His Cys Gln Val Leu Leu Leu Pro Leu
1370                1375                1380

Phe Ala Glu Cys His Lys Val Leu Ala Pro Ala Thr Phe Tyr Ala
1385                1390                1395

Ile Cys Gln Gln Asp Ser Cys His Gln Glu Gln Val Cys Glu Val
1400                1405                1410

Ile Ala Ser Tyr Ala His Leu Cys Arg Thr Asn Gly Val Cys Val
1415                1420                1425

Asp Trp Arg Thr Pro Asp Phe Cys Ala Met Ser Cys Pro Pro Ser
1430                1435                1440

Leu Val Tyr Asn His Cys Glu His Gly Cys Pro Arg His Cys Asp
1445                1450                1455

Gly Asn Val Ser Ser Cys Gly Asp His Pro Ser Glu Gly Cys Phe
1460                1465                1470

Cys Pro Pro Asp Lys Val Met Leu Glu Gly Ser Cys Val Pro Glu
1475                1480                1485

Glu Ala Cys Thr Gln Cys Ile Gly Glu Asp Gly Val Gln His Gln
1490                1495                1500

Phe Leu Glu Ala Trp Val Pro Asp His Gln Pro Cys Gln Ile Cys
1505                1510                1515

Thr Cys Leu Ser Gly Arg Lys Val Asn Cys Thr Thr Gln Pro Cys
1520                1525                1530

Pro Thr Ala Lys Ala Pro Thr Cys Gly Leu Cys Glu Val Ala Arg
1535                1540                1545

Leu Arg Gln Asn Ala Asp Gln Cys Cys Pro Glu Tyr Glu Cys Val
1550                1555                1560

Cys Asp Pro Val Ser Cys Asp Leu Pro Pro Val Pro His Cys Glu
```

```
                    1565                1570                1575
Arg Gly Leu Gln Pro Thr Leu Thr Asn Pro Gly Glu Cys Arg Pro
    1580                1585                1590

Asn Phe Thr Cys Ala Cys Arg Lys Glu Cys Lys Arg Val Ser
    1595                1600                1605

Pro Pro Ser Cys Pro Pro His Arg Leu Pro Thr Leu Arg Lys Thr
    1610                1615                1620

Gln Cys Cys Asp Glu Tyr Glu Cys Ala Cys Asn Cys Val Asn Ser
    1625                1630                1635

Thr Val Ser Cys Pro Leu Gly Tyr Leu Ala Ser Thr Ala Thr Asn
    1640                1645                1650

Asp Cys Gly Cys Thr Thr Thr Cys Leu Pro Asp Lys Val Cys
    1655                1660                1665

Val His Arg Ser Thr Ile Tyr Pro Val Gly Gln Phe Trp Glu Glu
    1670                1675                1680

Gly Cys Asp Val Cys Thr Cys Thr Asp Met Glu Asp Ala Val Met
    1685                1690                1695

Gly Leu Arg Val Ala Gln Cys Ser Gln Lys Pro Cys Glu Asp Ser
    1700                1705                1710

Cys Arg Ser Gly Phe Thr Tyr Val Leu His Glu Gly Glu Cys Cys
    1715                1720                1725

Gly Arg Cys Leu Pro Ser Ala Cys Glu Val Val Thr Gly Ser Pro
    1730                1735                1740

Arg Gly Asp Ser Gln Ser Ser Trp Lys Ser Val Gly Ser Gln Trp
    1745                1750                1755

Ala Ser Pro Glu Asn Pro Cys Leu Ile Asn Glu Cys Val Arg Val
    1760                1765                1770

Lys Glu Glu Val Phe Ile Gln Gln Arg Asn Val Ser Cys Pro Gln
    1775                1780                1785

Leu Glu Val Pro Val Cys Pro Ser Gly Phe Gln Leu Ser Cys Lys
    1790                1795                1800

Thr Ser Ala Cys Cys Pro Ser Cys Arg Cys Glu Arg Met Glu Ala
    1805                1810                1815

Cys Met Leu Asn Gly Thr Val Ile Gly Pro Gly Lys Thr Val Met
    1820                1825                1830

Ile Asp Val Cys Thr Thr Cys Arg Cys Met Val Gln Val Gly Val
    1835                1840                1845

Ile Ser Gly Phe Lys Leu Glu Cys Arg Lys Thr Thr Cys Asn Pro
    1850                1855                1860

Cys Pro Leu Gly Tyr Lys Glu Glu Asn Asn Thr Gly Glu Cys Cys
    1865                1870                1875

Gly Arg Cys Leu Pro Thr Ala Cys Thr Ile Gln Leu Arg Gly Gly
    1880                1885                1890

Gln Ile Met Thr Leu Lys Arg Asp Glu Thr Leu Gln Asp Gly Cys
    1895                1900                1905

Asp Thr His Phe Cys Lys Val Asn Glu Arg Gly Glu Tyr Phe Trp
    1910                1915                1920

Glu Lys Arg Val Thr Gly Cys Pro Pro Phe Asp Glu His Lys Cys
    1925                1930                1935

Leu Ala Glu Gly Gly Lys Ile Met Lys Ile Pro Gly Thr Cys Cys
    1940                1945                1950

Asp Thr Cys Glu Glu Pro Glu Cys Asn Asp Ile Thr Ala Arg Leu
    1955                1960                1965
```

```
Gln Tyr Val Lys Val Gly Ser Cys Lys Ser Glu Val Glu Val Asp
    1970            1975                1980

Ile His Tyr Cys Gln Gly Lys Cys Ala Ser Lys Ala Met Tyr Ser
    1985            1990                1995

Ile Asp Ile Asn Asp Val Gln Asp Gln Cys Ser Cys Cys Ser Pro
    2000            2005                2010

Thr Arg Thr Glu Pro Met Gln Val Ala Leu His Cys Thr Asn Gly
    2015            2020                2025

Ser Val Val Tyr His Glu Val Leu Asn Ala Met Glu Cys Lys Cys
    2030            2035                2040

Ser Pro Arg Lys Cys Ser Lys
    2045            2050

<210> SEQ ID NO 5
<211> LENGTH: 102
<212> TYPE: PRT
<213> ORGANISM: artificial sequence
<220> FEATURE:
<223> OTHER INFORMATION: Modified D' domain of VWF

<400> SEQUENCE: 5

Gly Leu Tyr Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala
            100

<210> SEQ ID NO 6
<211> LENGTH: 102
<212> TYPE: PRT
<213> ORGANISM: artificial sequence
<220> FEATURE:
<223> OTHER INFORMATION: Modified D' domain of VWF

<400> SEQUENCE: 6

Pro Leu Ile Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala
```

<210> SEQ ID NO 7
<211> LENGTH: 102
<212> TYPE: PRT
<213> ORGANISM: artificial sequence
<220> FEATURE:
<223> OTHER INFORMATION: Modified D' domain of VWF

<400> SEQUENCE: 7

Pro Leu Met Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala
            100

<210> SEQ ID NO 8
<211> LENGTH: 102
<212> TYPE: PRT
<213> ORGANISM: artificial sequence
<220> FEATURE:
<223> OTHER INFORMATION: Modified D' domain of VWF

<400> SEQUENCE: 8

Val Leu Tyr Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala
            100

<210> SEQ ID NO 9
<211> LENGTH: 102
<212> TYPE: PRT
<213> ORGANISM: artificial sequence
<220> FEATURE:
<223> OTHER INFORMATION: Modified D' domain of VWF

<400> SEQUENCE: 9

Glu Leu Tyr Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

```
Asp Leu Glu Cys Met Ser Met Gly Cys Val Ser Gly Cys Leu Cys Pro
            35                  40                  45

Pro Gly Met Val Arg His Glu Asn Arg Cys Val Ala Leu Glu Arg Cys
        50                  55                  60

Pro Cys Phe His Gln Gly Lys Glu Tyr Ala Pro Gly Glu Thr Val Lys
 65                  70                  75                  80

Ile Gly Cys Asn Thr Cys Val Cys Arg Asp Arg Lys Trp Asn Cys Thr
                85                  90                  95

Asp His Val Cys Asp Ala
            100

<210> SEQ ID NO 10
<211> LENGTH: 102
<212> TYPE: PRT
<213> ORGANISM: artificial sequence
<220> FEATURE:
<223> OTHER INFORMATION: Modified D' domain of VWF

<400> SEQUENCE: 10

Tyr Leu Tyr Cys Arg Pro Pro Met Val Lys Leu Val Cys Pro Ala Asp
 1               5                  10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
            35                  40                  45

Pro Gly Met Val Arg His Glu Asn Arg Cys Val Ala Leu Glu Arg Cys
        50                  55                  60

Pro Cys Phe His Gln Gly Lys Glu Tyr Ala Pro Gly Glu Thr Val Lys
 65                  70                  75                  80

Ile Gly Cys Asn Thr Cys Val Cys Arg Asp Arg Lys Trp Asn Cys Thr
                85                  90                  95

Asp His Val Cys Asp Ala
            100

<210> SEQ ID NO 11
<211> LENGTH: 102
<212> TYPE: PRT
<213> ORGANISM: artificial sequence
<220> FEATURE:
<223> OTHER INFORMATION: Modified D' domain of VWF

<400> SEQUENCE: 11

Leu Leu Tyr Cys Arg Pro Pro Met Val Lys Leu Val Cys Pro Ala Asp
 1               5                  10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
            35                  40                  45

Pro Gly Met Val Arg His Glu Asn Arg Cys Val Ala Leu Glu Arg Cys
        50                  55                  60

Pro Cys Phe His Gln Gly Lys Glu Tyr Ala Pro Gly Glu Thr Val Lys
 65                  70                  75                  80

Ile Gly Cys Asn Thr Cys Val Cys Arg Asp Arg Lys Trp Asn Cys Thr
                85                  90                  95

Asp His Val Cys Asp Ala
            100
```

```
<210> SEQ ID NO 12
<211> LENGTH: 102
<212> TYPE: PRT
<213> ORGANISM: artificial sequence
<220> FEATURE:
<223> OTHER INFORMATION: Modified D' domain of VWF

<400> SEQUENCE: 12

Pro Leu Trp Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala
            100

<210> SEQ ID NO 13
<211> LENGTH: 102
<212> TYPE: PRT
<213> ORGANISM: artificial sequence
<220> FEATURE:
<223> OTHER INFORMATION: Modified D' domain of VWF

<400> SEQUENCE: 13

Ser Leu Trp Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ala Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala
            100

<210> SEQ ID NO 14
<211> LENGTH: 102
<212> TYPE: PRT
<213> ORGANISM: artificial sequence
<220> FEATURE:
<223> OTHER INFORMATION: Modified D' domain of VWF

<400> SEQUENCE: 14

Ser Leu Tyr Cys Arg Lys Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45
```

```
Pro Gly Met Val Arg His Glu Asn Arg Cys Val Ala Leu Glu Arg Cys
        50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala
            100

<210> SEQ ID NO 15
<211> LENGTH: 102
<212> TYPE: PRT
<213> ORGANISM: artificial sequence
<220> FEATURE:
<223> OTHER INFORMATION: Modified D' domain of VWF

<400> SEQUENCE: 15

Ser Leu Tyr Cys Arg Asn Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
        50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala
            100

<210> SEQ ID NO 16
<211> LENGTH: 102
<212> TYPE: PRT
<213> ORGANISM: artificial sequence
<220> FEATURE:
<223> OTHER INFORMATION: Modified D' domain of VWF

<400> SEQUEN

```
<213> ORGANISM: artificial sequence
<220> FEATURE:
<223> OTHER INFORMATION: Modified D' domain of VWF

<400> SEQUENCE: 17

Pro Leu Leu Cys Arg Arg Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala
            100

<210> SEQ ID NO 18
<211> LENGTH: 2332
<212> TYPE: PRT
<213> ORGANISM: Homo sapiens

<400> SEQUENCE: 18

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240
```

```
Ser Leu Pro Gly Leu Ile Gly Cys His Arg Lys Ser Val Tyr Trp His
            245                 250                 255
Val Ile Gly Met Gly Thr Thr Pro Glu Val His Ser Ile Phe Leu Glu
        260                 265                 270
Gly His Thr Phe Leu Val Arg Asn His Arg Gln Ala Ser Leu Glu Ile
            275                 280                 285
Ser Pro Ile Thr Phe Leu Thr Ala Gln Thr Leu Leu Met Asp Leu Gly
    290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Glu Pro Gln Leu Arg
                325                 330                 335
Met Lys Asn Asn Glu Glu Ala Glu Asp Tyr Asp Asp Asp Leu Thr Asp
            340                 345                 350
Ser Glu Met Asp Val Val Arg Phe Asp Asp Asp Asn Ser Pro Ser Phe
        355                 360                 365
Ile Gln Ile Arg Ser Val Ala Lys Lys His Pro Lys Thr Trp Val His
    370                 375                 380
Tyr Ile Ala Ala Glu Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Lys Val Arg Phe Met Ala Tyr Thr
            420                 425                 430
Asp Glu Thr Phe Lys Thr Arg Glu Ala Ile Gln His Glu Ser Gly Ile
        435                 440                 445
Leu Gly Pro Leu Leu Tyr Gly Glu Val Gly Asp Thr Leu Leu Ile Ile
    450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
            500                 505                 510
Trp Thr Val Thr Val Glu Asp Gly Pro Thr Lys Ser Asp Pro Arg Cys
        515                 520                 525
Leu Thr Arg Tyr Tyr Ser Ser Phe Val Asn Met Glu Arg Asp Leu Ala
    530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
            580                 585                 590
Arg Phe Leu Pro Asn Pro Ala Gly Val Gln Leu Glu Asp Pro Glu Phe
        595                 600                 605
Gln Ala Ser Asn Ile Met His Ser Ile Asn Gly Tyr Val Phe Asp Ser
    610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
                645                 650                 655
```

-continued

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
        690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Ser Lys Asn Asn Ala
                725                 730                 735

Ile Glu Pro Arg Ser Phe Ser Gln Asn Ser Arg His Arg Ser Thr Arg
        740                 745                 750

Gln Lys Gln Phe Asn Ala Thr Thr Ile Pro Glu Asn Asp Ile Glu Lys
        755                 760                 765

Thr Asp Pro Trp Phe Ala His Arg Thr Pro Met Pro Lys Ile Gln Asn
        770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
                820                 825                 830

Glu Met Thr His Phe Arg Pro Gln Leu His His Ser Gly Asp Met Val
                835                 840                 845

Phe Thr Pro Glu Ser Gly Leu Gln Leu Arg Leu Asn Glu Lys Leu Gly
850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
        900                 905                 910

Tyr Asp Ser Gln Leu Asp Thr Thr Leu Phe Gly Lys Lys Ser Ser Pro
        915                 920                 925

Leu Thr Glu Ser Gly Gly Pro Leu Ser Leu Ser Glu Glu Asn Asn Asp
        930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
        980                 985                 990

Val Ser Ile Ser Leu Leu Lys Thr Asn Lys Thr Ser Asn Asn Ser Ala
        995                 1000                 1005

Thr Asn Arg Lys Thr His Ile Asp Gly Pro Ser Leu Leu Ile Glu
        1010                 1015                 1020

Asn Ser Pro Ser Val Trp Gln Asn Ile Leu Glu Ser Asp Thr Glu
        1025                 1030                 1035

Phe Lys Lys Val Thr Pro Leu Ile His Asp Arg Met Leu Met Asp
        1040                 1045                 1050

Lys Asn Ala Thr Ala Leu Arg Leu Asn His Met Ser Asn Lys Thr
        1055                 1060                 1065

Thr Ser Ser Lys Asn Met Glu Met Val Gln Gln Lys Lys Glu Gly

```
                1070                1075                1080
Pro Ile Pro Pro Asp Ala Gln Asn Pro Asp Met Ser Phe Phe Lys
        1085                1090                1095
Met Leu Phe Leu Pro Glu Ser Ala Arg Trp Ile Gln Arg Thr His
        1100                1105                1110
Gly Lys Asn Ser Leu Asn Ser Gly Gln Gly Pro Ser Pro Lys Gln
        1115                1120                1125
Leu Val Ser Leu Gly Pro Glu Lys Ser Val Glu Gly Gln Asn Phe
        1130                1135                1140
Leu Ser Glu Lys Asn Lys Val Val Val Gly Lys Gly Glu Phe Thr
        1145                1150                1155
Lys Asp Val Gly Leu Lys Glu Met Val Phe Pro Ser Ser Arg Asn
        1160                1165                1170
Leu Phe Leu Thr Asn Leu Asp Asn Leu His Glu Asn Asn Thr His
        1175                1180                1185
Asn Gln Glu Lys Lys Ile Gln Glu Glu Ile Glu Lys Lys Glu Thr
        1190                1195                1200
Leu Ile Gln Glu Asn Val Val Leu Pro Gln Ile His Thr Val Thr
        1205                1210                1215
Gly Thr Lys Asn Phe Met Lys Asn Leu Phe Leu Leu Ser Thr Arg
        1220                1225                1230
Gln Asn Val Glu Gly Ser Tyr Asp Gly Ala Tyr Ala Pro Val Leu
        1235                1240                1245
Gln Asp Phe Arg Ser Leu Asn Asp Ser Thr Asn Arg Thr Lys Lys
        1250                1255                1260
His Thr Ala His Phe Ser Lys Lys Gly Glu Glu Glu Asn Leu Glu
        1265                1270                1275
Gly Leu Gly Asn Gln Thr Lys Gln Ile Val Glu Lys Tyr Ala Cys
        1280                1285                1290
Thr Thr Arg Ile Ser Pro Asn Thr Ser Gln Gln Asn Phe Val Thr
        1295                1300                1305
Gln Arg Ser Lys Arg Ala Leu Lys Gln Phe Arg Leu Pro Leu Glu
        1310                1315                1320
Glu Thr Glu Leu Glu Lys Arg Ile Ile Val Asp Asp Thr Ser Thr
        1325                1330                1335
Gln Trp Ser Lys Asn Met Lys His Leu Thr Pro Ser Thr Leu Thr
        1340                1345                1350
Gln Ile Asp Tyr Asn Glu Lys Glu Lys Gly Ala Ile Thr Gln Ser
        1355                1360                1365
Pro Leu Ser Asp Cys Leu Thr Arg Ser His Ser Ile Pro Gln Ala
        1370                1375                1380
Asn Arg Ser Pro Leu Pro Ile Ala Lys Val Ser Ser Phe Pro Ser
        1385                1390                1395
Ile Arg Pro Ile Tyr Leu Thr Arg Val Leu Phe Gln Asp Asn Ser
        1400                1405                1410
Ser His Leu Pro Ala Ala Ser Tyr Arg Lys Lys Asp Ser Gly Val
        1415                1420                1425
Gln Glu Ser Ser His Phe Leu Gln Gly Ala Lys Lys Asn Asn Leu
        1430                1435                1440
Ser Leu Ala Ile Leu Thr Leu Glu Met Thr Gly Asp Gln Arg Glu
        1445                1450                1455
Val Gly Ser Leu Gly Thr Ser Ala Thr Asn Ser Val Thr Tyr Lys
        1460                1465                1470
```

```
Lys Val Glu Asn Thr Val Leu Pro Lys Pro Asp Leu Pro Lys Thr
1475                1480                1485

Ser Gly Lys Val Glu Leu Leu Pro Lys Val His Ile Tyr Gln Lys
1490                1495                1500

Asp Leu Phe Pro Thr Glu Thr Ser Asn Gly Ser Pro Gly His Leu
1505                1510                1515

Asp Leu Val Glu Gly Ser Leu Leu Gln Gly Thr Glu Gly Ala Ile
1520                1525                1530

Lys Trp Asn Glu Ala Asn Arg Pro Gly Lys Val Pro Phe Leu Arg
1535                1540                1545

Val Ala Thr Glu Ser Ser Ala Lys Thr Pro Ser Lys Leu Leu Asp
1550                1555                1560

Pro Leu Ala Trp Asp Asn His Tyr Gly Thr Gln Ile Pro Lys Glu
1565                1570                1575

Glu Trp Lys Ser Gln Glu Lys Ser Pro Glu Lys Thr Ala Phe Lys
1580                1585                1590

Lys Lys Asp Thr Ile Leu Ser Leu Asn Ala Cys Glu Ser Asn His
1595                1600                1605

Ala Ile Ala Ala Ile Asn Glu Gly Gln Asn Lys Pro Glu Ile Glu
1610                1615                1620

Val Thr Trp Ala Lys Gln Gly Arg Thr Glu Arg Leu Cys Ser Gln
1625                1630                1635

Asn Pro Pro Val Leu Lys Arg His Gln Arg Glu Ile Thr Arg Thr
1640                1645                1650

Thr Leu Gln Ser Asp Gln Glu Glu Ile Asp Tyr Asp Asp Thr Ile
1655                1660                1665

Ser Val Glu Met Lys Lys Glu Asp Phe Asp Ile Tyr Asp Glu Asp
1670                1675                1680

Glu Asn Gln Ser Pro Arg Ser Phe Gln Lys Lys Thr Arg His Tyr
1685                1690                1695

Phe Ile Ala Ala Val Glu Arg Leu Trp Asp Tyr Gly Met Ser Ser
1700                1705                1710

Ser Pro His Val Leu Arg Asn Arg Ala Gln Ser Gly Ser Val Pro
1715                1720                1725

Gln Phe Lys Lys Val Val Phe Gln Glu Phe Thr Asp Gly Ser Phe
1730                1735                1740

Thr Gln Pro Leu Tyr Arg Gly Glu Leu Asn Glu His Leu Gly Leu
1745                1750                1755

Leu Gly Pro Tyr Ile Arg Ala Glu Val Glu Asp Asn Ile Met Val
1760                1765                1770

Thr Phe Arg Asn Gln Ala Ser Arg Pro Tyr Ser Phe Tyr Ser Ser
1775                1780                1785

Leu Ile Ser Tyr Glu Glu Asp Gln Arg Gln Gly Ala Glu Pro Arg
1790                1795                1800

Lys Asn Phe Val Lys Pro Asn Glu Thr Lys Thr Tyr Phe Trp Lys
1805                1810                1815

Val Gln His His Met Ala Pro Thr Lys Asp Glu Phe Asp Cys Lys
1820                1825                1830

Ala Trp Ala Tyr Phe Ser Asp Val Asp Leu Glu Lys Asp Val His
1835                1840                1845

Ser Gly Leu Ile Gly Pro Leu Leu Val Cys His Thr Asn Thr Leu
1850                1855                1860
```

```
Asn Pro Ala His Gly Arg Gln Val Thr Val Gln Glu Phe Ala Leu
    1865            1870                1875

Phe Phe Thr Ile Phe Asp Glu Thr Lys Ser Trp Tyr Phe Thr Glu
    1880            1885                1890

Asn Met Glu Arg Asn Cys Arg Ala Pro Cys Asn Ile Gln Met Glu
    1895            1900                1905

Asp Pro Thr Phe Lys Glu Asn Tyr Arg Phe His Ala Ile Asn Gly
    1910            1915                1920

Tyr Ile Met Asp Thr Leu Pro Gly Leu Val Met Ala Gln Asp Gln
    1925            1930                1935

Arg Ile Arg Trp Tyr Leu Leu Ser Met Gly Ser Asn Glu Asn Ile
    1940            1945                1950

His Ser Ile His Phe Ser Gly His Val Phe Thr Val Arg Lys Lys
    1955            1960                1965

Glu Glu Tyr Lys Met Ala Leu Tyr Asn Leu Tyr Pro Gly Val Phe
    1970            1975                1980

Glu Thr Val Glu Met Leu Pro Ser Lys Ala Gly Ile Trp Arg Val
    1985            1990                1995

Glu Cys Leu Ile Gly Glu His Leu His Ala Gly Met Ser Thr Leu
    2000            2005                2010

Phe Leu Val Tyr Ser Asn Lys Cys Gln Thr Pro Leu Gly Met Ala
    2015            2020                2025

Ser Gly His Ile Arg Asp Phe Gln Ile Thr Ala Ser Gly Gln Tyr
    2030            2035                2040

Gly Gln Trp Ala Pro Lys Leu Ala Arg Leu His Tyr Ser Gly Ser
    2045            2050                2055

Ile Asn Ala Trp Ser Thr Lys Glu Pro Phe Ser Trp Ile Lys Val
    2060            2065                2070

Asp Leu Leu Ala Pro Met Ile Ile His Gly Ile Lys Thr Gln Gly
    2075            2080                2085

Ala Arg Gln Lys Phe Ser Ser Leu Tyr Ile Ser Gln Phe Ile Ile
    2090            2095                2100

Met Tyr Ser Leu Asp Gly Lys Lys Trp Gln Thr Tyr Arg Gly Asn
    2105            2110                2115

Ser Thr Gly Thr Leu Met Val Phe Phe Gly Asn Val Asp Ser Ser
    2120            2125                2130

Gly Ile Lys His Asn Ile Phe Asn Pro Pro Ile Ile Ala Arg Tyr
    2135            2140                2145

Ile Arg Leu His Pro Thr His Tyr Ser Ile Arg Ser Thr Leu Arg
    2150            2155                2160

Met Glu Leu Met Gly Cys Asp Leu Asn Ser Cys Ser Met Pro Leu
    2165            2170                2175

Gly Met Glu Ser Lys Ala Ile Ser Asp Ala Gln Ile Thr Ala Ser
    2180            2185                2190

Ser Tyr Phe Thr Asn Met Phe Ala Thr Trp Ser Pro Ser Lys Ala
    2195            2200                2205

Arg Leu His Leu Gln Gly Arg Ser Asn Ala Trp Arg Pro Gln Val
    2210            2215                2220

Asn Asn Pro Lys Glu Trp Leu Gln Val Asp Phe Gln Lys Thr Met
    2225            2230                2235

Lys Val Thr Gly Val Thr Thr Gln Gly Val Lys Ser Leu Leu Thr
    2240            2245                2250

Ser Met Tyr Val Lys Glu Phe Leu Ile Ser Ser Ser Gln Asp Gly
```

-continued

```
                2255                2260                2265
        His  Gln  Trp  Thr  Leu  Phe  Phe  Gln  Asn  Gly  Lys  Val  Lys  Val  Phe
                2270                2275                2280

Gln  Gly  Asn  Gln  Asp  Ser  Phe  Thr  Pro  Val  Val  Asn  Ser  Leu  Asp
                2285                2290                2295

Pro  Pro  Leu  Leu  Thr  Arg  Tyr  Leu  Arg  Ile  His  Pro  Gln  Ser  Trp
                2300                2305                2310

Val  His  Gln  Ile  Ala  Leu  Arg  Met  Glu  Val  Leu  Gly  Cys  Glu  Ala
                2315                2320                2325

Gln  Asp  Leu  Tyr
                2330

<210> SEQ ID NO 19
<211> LENGTH: 1444
<212> TYPE: PRT
<213> ORGANISM: artificial sequence
<220> FEATURE:
<223> OTHER INFORMATION: mature single chain Factor VIII

<400> SEQUENCE: 19

Ala  Thr  Arg  Arg  Tyr  Tyr  Leu  Gly  Ala  Val  Glu  Leu  Ser  Trp  Asp  Tyr
1                 5                  10                  15

Met  Gln  Ser  Asp  Leu  Gly  Glu  Leu  Pro  Val  Asp  Ala  Arg  Phe  Pro  Pro
                20                  25                  30

Arg  Val  Pro  Lys  Ser  Phe  Pro  Phe  Asn  Thr  Ser  Val  Val  Tyr  Lys  Lys
            35                  40                  45

Thr  Leu  Phe  Val  Glu  Phe  Thr  Asp  His  Leu  Phe  Asn  Ile  Ala  Lys  Pro
        50                  55                  60

Arg  Pro  Pro  Trp  Met  Gly  Leu  Leu  Gly  Pro  Thr  Ile  Gln  Ala  Glu  Val
65                  70                  75                  80

Tyr  Asp  Thr  Val  Val  Ile  Thr  Leu  Lys  Asn  Met  Ala  Ser  His  Pro  Val
                85                  90                  95

Ser  Leu  His  Ala  Val  Gly  Val  Ser  Tyr  Trp  Lys  Ala  Ser  Glu  Gly  Ala
                100                 105                 110

Glu  Tyr  Asp  Asp  Gln  Thr  Ser  Gln  Arg  Glu  Lys  Glu  Asp  Asp  Lys  Val
            115                 120                 125

Phe  Pro  Gly  Gly  Ser  His  Thr  Tyr  Val  Trp  Gln  Val  Leu  Lys  Glu  Asn
        130                 135                 140

Gly  Pro  Met  Ala  Ser  Asp  Pro  Leu  Cys  Leu  Thr  Tyr  Ser  Tyr  Leu  Ser
145                 150                 155                 160

His  Val  Asp  Leu  Val  Lys  Asp  Leu  Asn  Ser  Gly  Leu  Ile  Gly  Ala  Leu
                165                 170                 175

Leu  Val  Cys  Arg  Glu  Gly  Ser  Leu  Ala  Lys  Glu  Lys  Thr  Gln  Thr  Leu
                180                 185                 190

His  Lys  Phe  Ile  Leu  Leu  Phe  Ala  Val  Phe  Asp  Glu  Gly  Lys  Ser  Trp
            195                 200                 205

His  Ser  Glu  Thr  Lys  Asn  Ser  Leu  Met  Gln  Asp  Arg  Asp  Ala  Ala  Ser
        210                 215                 220

Ala  Arg  Ala  Trp  Pro  Lys  Met  His  Thr  Val  Asn  Gly  Tyr  Val  Asn  Arg
225                 230                 235                 240

Ser  Leu  Pro  Gly  Leu  Ile  Gly  Cys  His  Arg  Lys  Ser  Val  Tyr  Trp  His
                245                 250                 255

Val  Ile  Gly  Met  Gly  Thr  Thr  Pro  Glu  Val  His  Ser  Ile  Phe  Leu  Glu
                260                 265                 270

Gly  His  Thr  Phe  Leu  Val  Arg  Asn  His  Arg  Gln  Ala  Ser  Leu  Glu  Ile
```

-continued

```
                275                 280                 285
Ser Pro Ile Thr Phe Leu Thr Ala Gln Thr Leu Leu Met Asp Leu Gly
290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Pro Gln Leu Arg
                325                 330                 335
Met Lys Asn Asn Glu Glu Ala Glu Asp Tyr Asp Asp Leu Thr Asp
                340                 345                 350
Ser Glu Met Asp Val Val Arg Phe Asp Asp Asn Ser Pro Ser Phe
                355                 360                 365
Ile Gln Ile Arg Ser Val Ala Lys Lys His Pro Lys Thr Trp Val His
370                 375                 380
Tyr Ile Ala Ala Glu Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Lys Val Arg Phe Met Ala Tyr Thr
                420                 425                 430
Asp Glu Thr Phe Lys Thr Arg Glu Ala Ile Gln His Glu Ser Gly Ile
                435                 440                 445
Leu Gly Pro Leu Leu Tyr Gly Glu Val Gly Asp Thr Leu Leu Ile Ile
                450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
                500                 505                 510
Trp Thr Val Thr Val Glu Asp Gly Pro Thr Lys Ser Asp Pro Arg Cys
                515                 520                 525
Leu Thr Arg Tyr Tyr Ser Ser Phe Val Asn Met Glu Arg Asp Leu Ala
530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
                580                 585                 590
Arg Phe Leu Pro Asn Pro Ala Gly Val Gln Leu Glu Asp Pro Glu Phe
                595                 600                 605
Gln Ala Ser Asn Ile Met His Ser Ile Asn Gly Tyr Val Phe Asp Ser
                610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
                645                 650                 655
Thr Phe Lys His Lys Met Val Tyr Glu Asp Thr Leu Thr Leu Phe Pro
                660                 665                 670
Phe Ser Gly Glu Thr Val Phe Met Ser Met Glu Asn Pro Gly Leu Trp
                675                 680                 685
Ile Leu Gly Cys His Asn Ser Asp Phe Arg Asn Arg Gly Met Thr Ala
                690                 695                 700
```

```
Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Ser Lys Asn Asn Ala
            725                 730                 735

Ile Glu Pro Arg Ser Phe Ser Gln Asn Ser Arg His Arg Ser Thr Arg
            740                 745                 750

Gln Lys Gln Phe Asn Ala Thr Thr Ile Pro Glu Asn Thr Thr Leu Gln
            755                 760                 765

Ser Asp Gln Glu Glu Ile Asp Tyr Asp Asp Thr Ile Ser Val Glu Met
770                 775                 780

Lys Lys Glu Asp Phe Asp Ile Tyr Asp Glu Asp Glu Asn Gln Ser Pro
785                 790                 795                 800

Arg Ser Phe Gln Lys Lys Thr Arg His Tyr Phe Ile Ala Ala Val Glu
            805                 810                 815

Arg Leu Trp Asp Tyr Gly Met Ser Ser Ser Pro His Val Leu Arg Asn
            820                 825                 830

Arg Ala Gln Ser Gly Ser Val Pro Gln Phe Lys Lys Val Val Phe Gln
            835                 840                 845

Glu Phe Thr Asp Gly Ser Phe Thr Gln Pro Leu Tyr Arg Gly Glu Leu
850                 855                 860

Asn Glu His Leu Gly Leu Leu Gly Pro Tyr Ile Arg Ala Glu Val Glu
865                 870                 875                 880

Asp Asn Ile Met Val Thr Phe Arg Asn Gln Ala Ser Arg Pro Tyr Ser
            885                 890                 895

Phe Tyr Ser Ser Leu Ile Ser Tyr Glu Glu Asp Gln Arg Gln Gly Ala
            900                 905                 910

Glu Pro Arg Lys Asn Phe Val Lys Pro Asn Glu Thr Lys Thr Tyr Phe
            915                 920                 925

Trp Lys Val Gln His His Met Ala Pro Thr Lys Asp Glu Phe Asp Cys
930                 935                 940

Lys Ala Trp Ala Tyr Phe Ser Asp Val Asp Leu Glu Lys Asp Val His
945                 950                 955                 960

Ser Gly Leu Ile Gly Pro Leu Leu Val Cys His Thr Asn Thr Leu Asn
            965                 970                 975

Pro Ala His Gly Arg Gln Val Thr Val Gln Glu Phe Ala Leu Phe Phe
            980                 985                 990

Thr Ile Phe Asp Glu Thr Lys Ser Trp Tyr Phe Thr Glu Asn Met Glu
            995                 1000                1005

Arg Asn Cys Arg Ala Pro Cys Asn Ile Gln Met Glu Asp Pro Thr
            1010                1015                1020

Phe Lys Glu Asn Tyr Arg Phe His Ala Ile Asn Gly Tyr Ile Met
            1025                1030                1035

Asp Thr Leu Pro Gly Leu Val Met Ala Gln Asp Gln Arg Ile Arg
            1040                1045                1050

Trp Tyr Leu Leu Ser Met Gly Ser Asn Glu Asn Ile His Ser Ile
            1055                1060                1065

His Phe Ser Gly His Val Phe Thr Val Arg Lys Lys Glu Glu Tyr
            1070                1075                1080

Lys Met Ala Leu Tyr Asn Leu Tyr Pro Gly Val Phe Glu Thr Val
            1085                1090                1095

Glu Met Leu Pro Ser Lys Ala Gly Ile Trp Arg Val Glu Cys Leu
            1100                1105                1110
```

```
Ile Gly Glu His Leu His Ala Gly Met Ser Thr Leu Phe Leu Val
    1115                1120                1125

Tyr Ser Asn Lys Cys Gln Thr Pro Leu Gly Met Ala Ser Gly His
    1130                1135                1140

Ile Arg Asp Phe Gln Ile Thr Ala Ser Gly Gln Tyr Gly Gln Trp
    1145                1150                1155

Ala Pro Lys Leu Ala Arg Leu His Tyr Ser Gly Ser Ile Asn Ala
    1160                1165                1170

Trp Ser Thr Lys Glu Pro Phe Ser Trp Ile Lys Val Asp Leu Leu
    1175                1180                1185

Ala Pro Met Ile Ile His Gly Ile Lys Thr Gln Gly Ala Arg Gln
    1190                1195                1200

Lys Phe Ser Ser Leu Tyr Ile Ser Gln Phe Ile Ile Met Tyr Ser
    1205                1210                1215

Leu Asp Gly Lys Lys Trp Gln Thr Tyr Arg Gly Asn Ser Thr Gly
    1220                1225                1230

Thr Leu Met Val Phe Phe Gly Asn Val Asp Ser Ser Gly Ile Lys
    1235                1240                1245

His Asn Ile Phe Asn Pro Pro Ile Ile Ala Arg Tyr Ile Arg Leu
    1250                1255                1260

His Pro Thr His Tyr Ser Ile Arg Ser Thr Leu Arg Met Glu Leu
    1265                1270                1275

Met Gly Cys Asp Leu Asn Ser Cys Ser Met Pro Leu Gly Met Glu
    1280                1285                1290

Ser Lys Ala Ile Ser Asp Ala Gln Ile Thr Ala Ser Ser Tyr Phe
    1295                1300                1305

Thr Asn Met Phe Ala Thr Trp Ser Pro Ser Lys Ala Arg Leu His
    1310                1315                1320

Leu Gln Gly Arg Ser Asn Ala Trp Arg Pro Gln Val Asn Asn Pro
    1325                1330                1335

Lys Glu Trp Leu Gln Val Asp Phe Gln Lys Thr Met Lys Val Thr
    1340                1345                1350

Gly Val Thr Thr Gln Gly Val Lys Ser Leu Leu Thr Ser Met Tyr
    1355                1360                1365

Val Lys Glu Phe Leu Ile Ser Ser Ser Gln Asp Gly His Gln Trp
    1370                1375                1380

Thr Leu Phe Phe Gln Asn Gly Lys Val Lys Val Phe Gln Gly Asn
    1385                1390                1395

Gln Asp Ser Phe Thr Pro Val Val Asn Ser Leu Asp Pro Pro Leu
    1400                1405                1410

Leu Thr Arg Tyr Leu Arg Ile His Pro Gln Ser Trp Val His Gln
    1415                1420                1425

Ile Ala Leu Arg Met Glu Val Leu Gly Cys Glu Ala Gln Asp Leu
    1430                1435                1440

Tyr

<210> SEQ ID NO 20
<211> LENGTH: 585
<212> TYPE: PRT
<213> ORGANISM: Homo sapiens

<400> SEQUENCE: 20

Asp Ala His Lys Ser Glu Val Ala His Arg Phe Lys Asp Leu Gly Glu
1               5                   10                  15
```

```
Glu Asn Phe Lys Ala Leu Val Leu Ile Ala Phe Ala Gln Tyr Leu Gln
                 20                  25                  30

Gln Cys Pro Phe Glu Asp His Val Lys Leu Val Asn Glu Val Thr Glu
             35                  40                  45

Phe Ala Lys Thr Cys Val Ala Asp Glu Ser Ala Glu Asn Cys Asp Lys
 50                  55                  60

Ser Leu His Thr Leu Phe Gly Asp Lys Leu Cys Thr Val Ala Thr Leu
65                   70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
            130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
```

```
                    435                 440                 445
Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
                515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
                580                 585
```